(12) United States Patent
Neumann

(10) Patent No.: US 10,990,884 B1
(45) Date of Patent: Apr. 27, 2021

(54) METHODS AND SYSTEMS FOR IDENTIFYING COMPATIBLE MEAL OPTIONS

(71) Applicant: Kenneth Neumann, Lakewood, CO (US)

(72) Inventor: Kenneth Neumann, Lakewood, CO (US)

(73) Assignee: KPN INNOVATIONS, LLC, Lakewood, CO (US)

( * ) Notice: Subject to any disclaimer, the term of this patent is extended or adjusted under 35 U.S.C. 154(b) by 0 days.

(21) Appl. No.: 16/659,817

(22) Filed: Oct. 22, 2019

(51) Int. Cl.
*G06N 5/04* (2006.01)
*G06F 16/25* (2019.01)
*G06N 20/00* (2019.01)
*G06F 16/28* (2019.01)

(52) U.S. Cl.
CPC ............. *G06N 5/04* (2013.01); *G06F 16/252* (2019.01); *G06F 16/285* (2019.01); *G06N 20/00* (2019.01)

(58) Field of Classification Search
CPC ........ G06N 5/04; G06N 20/00; G06F 16/285; G06F 16/252
See application file for complete search history.

(56) References Cited

U.S. PATENT DOCUMENTS

| | | | |
|---|---|---|---|
| 8,601,005 B2 | 12/2013 | Bousamra et al. | |
| 8,762,167 B2 | 6/2014 | Blander et al. | |
| 10,325,685 B2 | 6/2019 | Apte et al. | |
| 2015/0228062 A1* | 8/2015 | Joshi | G06F 16/583 382/110 |
| 2017/0286625 A1* | 10/2017 | Blander | A61B 5/0245 |
| 2018/0144821 A1 | 5/2018 | Irani-Cohen et al. | |

(Continued)

OTHER PUBLICATIONS

Sideris et al., "A flexible data-driven comorbidity feature extraction framework", 2016, all pages (Year: 2016).*

(Continued)

*Primary Examiner* — Daniel C Puentes
(74) *Attorney, Agent, or Firm* — Caldwell Intellectual Property Law

(57) ABSTRACT

A system for identifying compatible meal options. The system includes a body analysis module configured to receive a user biological marker, select a clustering dataset from a clustering database, generate a hierarchical clustering algorithm and assign a plurality of user body measurements to a first classified dataset cluster. The system includes a food analysis module configured to select a food training set from a food database, generate using a supervised machine-learning process a food model, generate a food tolerance instruction set, and display on a graphical user interface the food tolerance instruction set. The system includes a menu generator module configured to select a menu training set from a menu database, generate using a supervised machine-learning process a menu model that produces an output containing a plurality of menu options, and display on a graphical user interface the plurality of menu options. The system includes a local selector module configured to receive a plurality of meal option inputs from a meal preparer device, generate a k-nearest neighbors algorithm, identify a plurality of compatible meal options, and display the plurality of compatible meal options on a graphical user interface.

20 Claims, 12 Drawing Sheets

(56) References Cited

U.S. PATENT DOCUMENTS

| | | |
|---|---|---|
| 2018/0240542 A1* | 8/2018 | Grimmer ............ G06F 16/9535 |
| 2019/0156925 A1 | 5/2019 | Martinez-Arocho et al. |
| 2019/0221303 A1 | 7/2019 | Bennett |
| 2019/0244541 A1* | 8/2019 | Hadad ................ G09B 19/0092 |
| 2019/0252058 A1 | 8/2019 | Wolf et al. |
| 2019/0290172 A1 | 9/2019 | Hadad et al. |

OTHER PUBLICATIONS

Phanich et al, "Food Recommendation System Using Clustering Analysis for Diabetic Patients", 2010 IEEE, all pages (Year: 2010).*

Bischoff et al, "Intestinal permeability—a new target for disease prevention and therapy", 2014, BMC Gastroenterology, all pages (Year: 2014).*

"The Pros and Cons of Personalized Nutrition"; Tony Tarver; Oct. 1, 2018; https://www.ift.org/news-and-publications/food-technology-magazine/issues/2018/october/features/customized-nutrition-tests retrieved Oct. 7, 2019.

"Precision Nutrition: A Review of Personalized Nutritional Approaches for the Prevention of Management of Metabolic Syndrome"; Toro-Martin et al.; Aug. 2017; https://www.ncbi.nlm.nih.gov/pmc/articles/PMC5579706/ retrieved Oct. 7, 2019.

* cited by examiner

METHODS AND SYSTEMS FOR IDENTIFYING COMPATIBLE MEAL OPTIONS

FIELD OF THE INVENTION

The present invention generally relates to the field of artificial intelligence. In particular, the present invention is directed to methods and systems for identifying compatible meal options.

BACKGROUND

Accurate identification of compatible meal options can be challenging. Analyzing multiple user demands and requirements can be complex. Further, this can be complicated by large quantities of data to be analyzed to locate and identify compatible meal options.

SUMMARY OF THE DISCLOSURE

In an aspect, a system for identifying compatible meal options. The system includes a processor wherein the processor further comprises a body analysis module wherein the body analysis module is further configured to receive a user biological marker wherein the user biological marker contains a plurality of user body measurements; select a clustering dataset from a clustering database wherein the clustering dataset further comprises a plurality of unclassified datapoints; generate a hierarchical clustering algorithm using the clustering dataset as input and wherein the hierarchical clustering algorithm outputs a definite number of classified dataset clusters each containing a cluster label; assign the plurality of user body measurements to a first classified dataset cluster containing a cluster label; and select the first classified dataset cluster containing the cluster label. The system includes a food analysis module wherein the food analysis module is further configured to receive from the body analysis module the first classified dataset cluster containing the cluster label and the user biological marker; select a food training set from a food database as a function of the user biological marker wherein the food training set correlates user body measurements to food tolerance scores; generate using a supervised machine-learning process a food model that receives the first assigned user body data element as an input and produces an output containing a food tolerance score; generate a food tolerance instruction set using the food tolerance score; and display on a graphical user interface located on the processor the output containing the food tolerance instruction set containing the food tolerance score. The system includes a menu generator module wherein the menu generator module is further configured to receive the food tolerance instruction set from the food analysis module; select a menu training set from a menu database as a function of the food tolerance instruction set wherein the menu training set correlates food tolerance scores to menu options; generate using a supervised machine-learning process a menu model that receives the food tolerance instruction set as an input and produces an output containing a plurality of menu options utilizing the menu training set; and display on the graphical user interface located on the processor the output containing the plurality of menu options. The system includes a local selector module wherein the local selector module is further configured to receive a plurality of meal option inputs from a meal preparer device wherein the meal option inputs contain available menu listings; receive the output containing the plurality of menu options from the menu generator module; generate a k-nearest neighbors algorithm utilizing the plurality of meal option inputs and the plurality of menu options; identify a plurality of compatible meal options as a function of generating the k-nearest neighbor algorithm; and display the plurality of compatible meal options on the graphical user interface located on the processor.

In an aspect, a method of identifying compatible meal options. the method includes receiving by a processor a user biological marker wherein the user biological marker contains a plurality of user body measurements. The method includes selecting by the processor a clustering dataset from a clustering database wherein the clustering dataset further comprises a plurality of unclassified datapoints. The method includes generating by the processor a hierarchical clustering algorithm using the clustering dataset as input and wherein the hierarchical clustering algorithm outputs a definite number of classified dataset clusters each containing a cluster label. The method includes assigning by the processor the plurality of user body measurements to a first classified dataset cluster containing a cluster label. The method includes selecting by the processor the first classified dataset cluster containing the cluster label. The method includes selecting by the processor a food training set from a food database as a function of the user biological marker wherein the food training set correlates user body measurements to food tolerance scores. The method includes generating by the processor using a supervised machine-learning process a food model that receives the first assigned user body data element as an input and produces an output containing a food tolerance score. The method includes generating by the processor a food tolerance instruction set using the food tolerance score. The method includes displaying by the processor on a graphical user interface the output containing the food tolerance instruction set containing the food tolerance score. The method includes selecting by the processor a menu training set from a menu database as a function of the food tolerance instruction set wherein the menu training set correlates food tolerance scores to menu options. The method includes generating by the processor using a supervised machine-learning process a menu model that receives the food tolerance instruction set as an input and produces an output containing a plurality of menu options utilizing the menu training set. The method includes displaying by the processor on the graphical user interface located the output containing the plurality of menu options. The method includes receiving by the processor a plurality of meal option inputs from a meal preparer device wherein the meal option inputs contain available menu listings. The method includes generating by the processor a k-nearest neighbors algorithm utilizing the plurality of meal option inputs and the plurality of menu options. The method includes identifying by the processor a plurality of compatible meal options as a function of generating the k-nearest neighbor algorithm. The method includes displaying by the processor the plurality of compatible meal options on the graphical user interface.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention.

However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to methods and systems for identifying compatible meal options. In an embodiment, a processor receives a user biological marker containing a plurality of user body measurements. A processor selects a clustering dataset from a clustering database and generates a hierarchical clustering algorithm to output a definite number of classified dataset clusters each containing a cluster label. A processor assigns a user biological marker containing a plurality of user body measurements to a first classified dataset clustering containing a cluster label. A processor selects a food training set from a food database as a function of a user biological marker. A food training set correlates user body measurements to food tolerance scores. A processor generates using a supervised machine-learning process a food model that receives the first assigned user body data element as input and produces an output containing a food tolerance score. A processor generates a food tolerance instruction set using a food tolerance score. A processor displays on a graphical user interface an output containing a food tolerance instruction set. A processor selects a menu training set from a menu database. A menu training set correlates food tolerance scores to menu options. A processor generates using a supervised machine-learning process a menu model that receives a food tolerance instruction set as an input and produces an output containing a plurality of menu options utilizing the menu training set. A processor displays on a graphical user interface an output containing a plurality of menu options. A processor receives a plurality of meal option inputs from a meal preparer device. A processor generates a k-nearest neighbors algorithm utilizing a plurality of meal option inputs and a plurality of menu options. A processor identifies a plurality of compatible meal options as a function of generating a k-nearest neighbor algorithm. A processor displays a plurality of compatible meal options on a graphical user interface.

Figure 1:
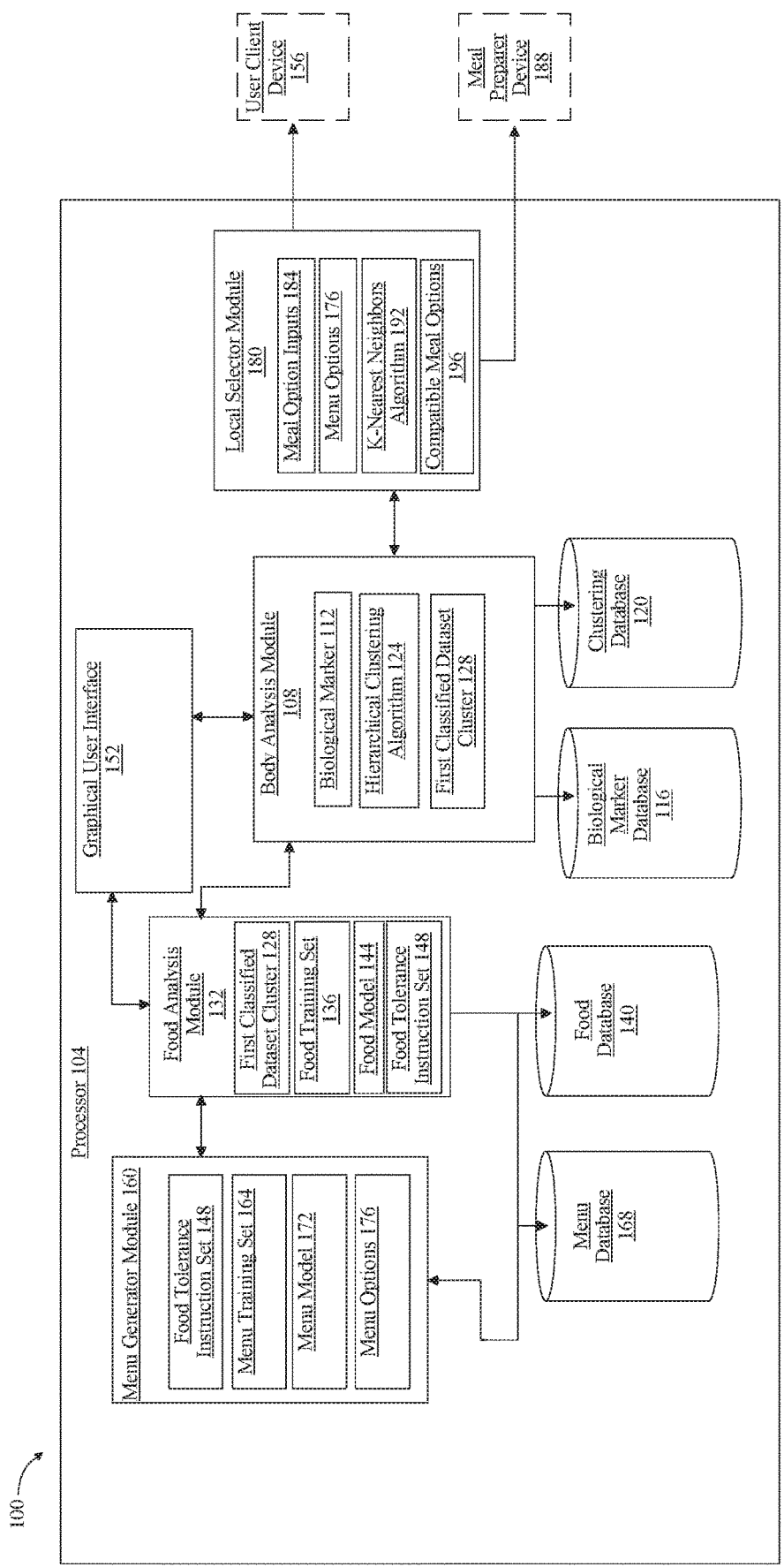
FIG. 1 is a block diagram illustrating an exemplary embodiment of a system for identifying compatible meal options.

Referring now to FIG. 1, an exemplary embodiment of a system 100 for identifying compatible meal options is illustrated. System 100 includes a processor 104. A processor 104 may include any computing device as described herein, including without limitation a microcontroller, microprocessor 104, digital signal processor 104 (DSP) and/or system on a chip (SoC) as described herein. A processor 104 may be housed with, may be incorporated in, or may incorporate one or more sensors of at least a sensor. Computing device may include, be included in, and/or communicate with a mobile device such as a mobile telephone or smartphone. A processor 104 may include a single computing device operating independently, or may include two or more computing device operating in concert, in parallel, sequentially or the like; two or more computing devices may be included together in a single computing device or in two or more computing devices. A processor 104 with one or more additional devices as described below in further detail via a network interface device. Network interface device may be utilized for connecting a processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. A processor 104 may include but is not limited to, for example, A processor 104 or cluster of computing devices in a first location and a second computing device or cluster of computing devices in a second location. A processor 104 may include one or more computing devices dedicated to data storage, security, distribution of traffic for load balancing, and the like. A processor 104 may distribute one or more computing tasks as described below across a plurality of computing devices of computing device, which may operate in parallel, in series, redundantly, or in any other manner used for distribution of tasks or memory between computing devices. A processor 104 may be implemented using a "shared nothing" architecture in which data is cached at the worker, in an embodiment, this may enable scalability of system 100 and/or computing device.

With continued reference to FIG. 1, a processor 104 may be designed and/or configured to perform any method, method step, or sequence of method steps in any embodiment described in this disclosure, in any order and with any degree of repetition. For instance, a processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A processor 104 may perform any step or sequence of steps as described in this disclosure in parallel, such as simultaneously and/or substantially simultaneously performing a step two or more times using two or more parallel threads, processor 104 cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, system 100 includes a body analysis module 108, which may be implemented as any hardware and/or software module. Body analysis module 108 is designed and configured receive a user biological marker 112 wherein the user biological marker 112 contains a plurality of user body measurements; select a clustering dataset from a clustering database 120 wherein the clustering dataset further comprises a plurality of unclassified datapoints; generate a hierarchical clustering algorithm 124 using the clustering dataset as input and wherein the hierarchical clustering algorithm 124 outputs a definite number of classified dataset clusters each containing a cluster label; assign the plurality of user body data elements to a first classified dataset cluster 128 containing a cluster label; and select a first assigned user body data element containing the cluster label.

With continued reference to FIG. 1, body analysis module 108 is configured to receive a user biological marker 112 from a biological marker database 112. A "user biological marker 112" as used in this disclosure, includes any element of physiological state data. Physiological data may include any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological data may be obtained from a physical sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like.

Continuing to refer to FIG. 1, user biological marker 112 contains a plurality of user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, *firmicutes, Bacteroidetes*, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, *cryptosporidium* EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *Clostridium difficile, Cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example *Firmicutes* species, *Bacteroidetes* species, *Proteobacteria* species, *Verrumicrobia* species, *Actinobacteria* species, *Fusobacteria* species, *Cyanobacteria* species and the like. Archaea may include methanogens such as *Methanobrevibacter smithies*' and *Methanosphaera stadtmanae*. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as *Ackerman's muciniphila, Anaerotruncus colihominis, bacteriology, Bacteroi-*

*des vulgates', Bacteroides-Prevotella, Barnesiella* species, *Bifidobacterium longarm, Bifidobacterium* species, *Butyrivbrio crossotus, Clostridium* species, *Collinsella aerofaciens,* fecal color, fecal consistency, *Coprococcus eutactus, Desulfovibrio piger, Escherichia coli, Faecalibacterium prausnitzii,* Fecal occult blood, *Firmicutes* to *Bacteroidetes* ratio, *Fusobacterium* species, *Lactobacillus* species, *Methanobrevibacter smithii,* yeast minimum inhibitory concentration, bacteria minimum inhibitory concentration, yeast mycology, fungi mycology, *Odoribacter* species, *Oxalobacter formigenes,* parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fulness after eating. Genetic body measurement may include MP4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androstereone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1.

With continued reference to FIG. 1, body analysis module 108 is configured to select a clustering dataset from a clustering database 120. A "clustering dataset" as used in this disclosure, is a dataset including a plurality of unclassified datapoints. A "datapoint" as used in this disclosure, includes a discrete unit of information. A datapoint may be derived from a measurement, research, and/or expert input. A datapoint may include one or more measurements on a single member of unit of observation. Datapoints may be stored in any suitable data and/or data type. For instance and without limitation, datapoints may include textual data, such as numerical, character, and/or string data. Textual data may include a standardized name and/or code for a disease, disorder, or the like, codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as dataset may take; persons skilled in the art, upon reviewing the entirety of this disclosure, will be aware of various forms which may be suitable for use as dataset consistently with this disclosure.

With continued reference to FIG. 1, clustering database 120 may include any data structure for ordered storage and retrieval of data, which may be implemented as a hardware or software module. Clustering database 120 may be implemented, without limitation, as a relational database, a key-value retrieval datastore such as a NO SQL database, or any other format or structure for use as a datastore that a person skilled in the art would recognize as suitable upon review of the entirety of this disclosure. Clustering database 120 may include one or more data entries containing one or more clustering datasets. Processor 104 and/or body analysis module 108 may select a clustering dataset from clustering database 120 by classifying a user body data element to a body dimension, generating a body dimension label, and selecting a clustering dataset by matching the body dimension label to a clustering dataset containing unclassified datapoints related to the body dimension label. A "body dimension" as used in this disclosure, includes one or more functional body systems that are impaired by disease in a human body and/or animal body. Functional body systems may include one or more body systems recognized as attributing to root causes of disease by functional medicine practitioners and experts. Body dimensions may include one or more of the body systems as described above including but not limited to microbiome, gut-wall, genetics, epigenetics, metabolic, nutrients, environment, toxicity, and the like. A "body dimension label" as used in this disclosure, includes a classification label identifying a particular body dimension. Classification label may be generated utilizing any methodology as described herein. Classifying a user body data element to a body dimension may include predicting the given body dimension that a user body data element may relate to. Classifying may include predictive modeling that may map an input variable such as a user body data element to a discrete output variable that includes a body dimension. Classification may be performed using lazy learners, eager learners, and/or classification algorithms that include decision trees, Naïve bayes, artificial neural networks, K-nearest neighbor (KNN) and the like as described in more detail below. For instance and without limitation, a user body data element such as positive presence of *Giardia lamblia* found in a user stool sample, may be classified to a body dimension such as gut-wall. Clustering datasets may be organized within clustering database 120 by body dimension and indicative as to what unclassified datapoints may relate to. For instance and without limitation, a clustering dataset that contains unclassified datapoints relating to particular genetic single nucleotide polymorphisms (SNPS) may be organized within clustering database 120 and contained within a data table relating to genetic body dimension. In an embodiment, a particular clustering dataset may be organized within clustering database 120 as relating to one or more body dimensions. Processor 104 and/or body analysis module 108 may match a generated body dimension label to a clustering dataset organized with clustering database 120 by comparing a body dimension label to a particular data table to see if they both match and are the same.

With continued reference to FIG. 1, body analysis module 108 is configured to generate a hierarchical clustering algorithm 124. A "hierarchical clustering algorithm" as used in this disclosure includes a method of cluster analysis that groups objects such as datapoints in a way that datapoints assigned to the same cluster are deemed to be more similar to each other than datapoints found in other clusters. Hierarchical clustering algorithm 124 may include an agglomerative or bottom-up approach where each observation may start in its own cluster and pairs of clusters are merged as one moves up the hierarchy. Hierarchical clustering algorithm 124 may include divisive or a top-down approach where all observations may start in one cluster and splits may be performed recursively as one moves down the hierarchy. Before clustering is performed, linkage measurements must be performed that determine a proximity matrix containing the distance between each datapoint using a distance function. The proximity matrix may then be updated to display the distance between each cluster. Linkage measurements may include complete linkage, where for each pair of clusters, the algorithm computes and merges them to minimize the maximum distance between the clusters. Linkage measurements may include average linkage, where the algorithm may use the average distance between the pairs of clusters. Linkage measurements may include ward's linkage where all clusters are considered, and the algorithm computes the sum of squared distances within the clusters and merges them to minimize it. Clusters that may be combined as in agglomerative hierarchical clustering or clusters that may be split as in divisive hierarchical clustering may be determined based on measuring dissimilarity between sets of observations. Dissimilarity may be measured utilizing a metric that may include but are not limited to Euclidean distance, squared Euclidean distance, Manhattan distance, maximum distance, Hamming distance, Levenshtein distance, and/or mahalanobis distance. Hierarchical clustering algorithm 124 may include assigning datapoints to separate clusters and then computing the distance or similarity between each of the clusters. Hierarchical clustering algorithm 124 outputs a definite number of classified dataset clusters each containing a cluster label. Each cluster is distinct from each other cluster and datapoints contained within each cluster are broadly similar to each other. Each output cluster contains a cluster label, which identifies the topic of each cluster and datapoints contained within a cluster and distinguish the clusters from each other. Cluster labels may be generated from terms that occur frequently within the centroid of a cluster. Cluster labels may be generated from title labels and/or external knowledge labels. Cluster labels may be displayed as textual data, image data, and the like. In an embodiment, cluster labels of several different cluster labelers may be combined to achieve defined and precise labels. For example, linear regression may be used to learn an optimal combination of labeler scores. In an embodiment, cluster label may indicate and describe a particular body dimension to be analyzed. Body analysis module 108 assigns the plurality of user body measurements to a first classified dataset cluster 128 containing a cluster label. Body analysis module 108 selects a first assigned user body data element containing the cluster label.

With continued reference to FIG. 1, system 100 includes a food analysis module 132, which may be implemented as any hardware and/or software module. Food analysis module 132 is designed and configured to receive the first assigned user body data element containing the cluster label from the body analysis module 108; select a food training set 136 from a food database 140 as a function of the user body data element wherein the food training set 136 correlates user body measurements to food tolerance scores; generate using a supervised machine-learning process a food model 144 that receives the first assigned user body data element as an input and produces an output containing a food tolerance score; generate a food tolerance instruction set 148 using the food tolerance score; and display on a graphical user interface 152 located on the processor 104 the output containing the food tolerance instruction set 148 containing the food tolerance score.

With continued reference to FIG. 1, food analysis module 132 selects a food training set 136 from a food database 140. Food training set is a set of training data. "Training data," as used in this disclosure, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by at least a server may correlate any input data as described in this disclosure to any output data as described in this disclosure.

With continued reference to FIG. 1, correlation in a training set may include any relation established therein linking one datum to another, including inclusion together in a data element, row, column, cell, or the like, and/or by giving each a common indicator and/or label indicative of their correlation in data used to create and/or compile training data. Correlation may include a relation established whereby user body measurements are correlated to food tolerance scores based on data entries obtained from the same subject. Training set may include a plurality of entries, each entry correlating at least an element of user body measurement data to food tolerance scores.

With continued reference to FIG. 1, food training set includes a plurality of data entries. Food training set includes at least an element of user body measurement correlated to food tolerance scores. For instance and without limitation, food training set may include a user body measurement such as a positive methane breath test correlated to a food tolerance score that indicates avoiding foods that include honey, agave nectar, lactose, wheat, apples, and pears and also indicates consuming superfoods such as buckwheat, kiwi, *quinoa*, millet, kale, chicken, and lamb and also indicates limiting foods that contain garlic and onion. In yet another non-limiting example, food training set may include a user body measurement such as a positive copy of a MSH6 or Lynch Syndrome gene correlated to a food tolerance score that indicates avoiding foods such as sausage, red meat, margarine, and soda and indicates consuming superfoods that include broccoli, kale, Brussel sprouts, onion, garlic, and leek and also indicates limiting foods that contain white sugar and products synthesized from corn.

With continued reference to FIG. 1, food analysis module 132 may select a food training set 136 from a food database 140. Food database 140 may include any data structure suitable for use as clustering database 120 as described above. Food database 140 may store food training set 136. Food analysis module 132 may select a food training set 136 from food database 140 as a function of user body data element wherein food training set 136 correlates user body measurements to food tolerance scores. For instance and without limitation, user body data element may include a blood sample containing an elevated hemoglobin A1C level. In such an instance, food analysis module 132 may select a food training set 136 from food database 140 containing a data entry that includes an elevated hemoglobin A1C level correlated to food tolerance scores. In yet another non-limiting example, user body data element may include a stool sample containing elevated levels of calprotectin released by white blood cells and linked to inflammation in the intestines. In such an instance, food analysis module 132 may select a food training set 136 from food database 140 containing a data entry that includes an elevated calprotectin level correlated to food tolerance scores.

With continued reference to FIG. 1, a "food tolerance score" as used in this disclosure includes an indication of a user ability to tolerate a particular food item. Tolerance includes a capacity of a human being to digest a particular food item. Food item may include any substance suitable for consumption by a human being. For instance and without limitation, food item may include a fruit such as banana, a vegetable such as kale, an animal product such as lamb, a protein such as tofu, an herb such as rosemary, a spice such as cinnamon and the like. Food tolerance score may include an indicator generated on a curve of tolerability that may include a particular category of tolerability such as food items that can be enjoyed without concern, food items that should be minimized and only consumed with regard to particular serving sizes, and food items that should be avoided due to an inability of the body to metabolize them and/or the contribution of particular food items to contribute to inflammation and gut dysbiosis. Food tolerance scores may include a numerical score that may indicate tolerance to a particular food item as reflected in a score between zero to one hundred, whereby a score with a higher value and closer to one hundred may reflect higher tolerance.

With continued reference to FIG. 1, food analysis module 132 is configured to generate using a supervised machine-learning process a food model 144 that receives the first assigned user body data element as an input and produces an output containing a food tolerance score. Food model 144 includes any machine learning process that is a linear or polynomial regression algorithm, the food model might be an equation; it might be a set of instructions to generate outputs based on inputs which is derived using the machine-learning algorithm, and the like. Supervised machine-learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of body measurements as inputs, food tolerance scores as outputs, and a scoring function representing a desired form of relationship to be detected between elements of body measurements and food tolerances; scoring function may, for instance, seek to maximize the probability that a given element of food tolerance is associated with a given food tolerance score and/or combination of food tolerance scores to minimize the probability that a given element of body measurement data and/or combination of elements of body measurement data is not associated with a given food tolerance score and/or combination of food tolerance scores. Scoring function may be expressed as a risk function representing an "expected loss" of an algorithm relating inputs to outputs, where loss is computed as an error function representing a degree to which a prediction generated by the relation is incorrect when compared to a given input-output pair provided in a training set. Persons skilled in the art, upon reviewing the entirety of this disclosure, will be aware of various possible variations of supervised machine-learning algorithms that may be used to determine relation between elements of body measurement data and food tolerance scores. In an embodiment, one or more supervised machine-learning algorithms may be restricted to a particular domain for instance, a supervised machine-learning process may be performed with respect to a given set of parameters and/or categories of parameters that have been suspected to be related to a given set of body measurements, and/or are specified as linked to a medical specialty and/or field of medicine covering a particular set of body measurement data. As a non-limiting example, a particular set of body measurements that indicate gut dysbiosis and *candida* overgrowth may be typically associated with a known intolerance to fermented foods such as sauerkraut, and a supervised machine-learning process may be performed to relate those body measurements to the various food intolerance scores; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate diagnostic data. Additional supervised learning processes may be performed without domain restrictions to detect, for instance, previously unknown and/or unsuspected relationships between body measurement data and food tolerance scores.

With continued reference to FIG. 1, food analysis module 132 is configured to generate a food tolerance instruction set 148 using a food tolerance score. A "food tolerance instruction set 148" as used in this disclosure, includes a data structure containing one or more food tolerance scores organized by particular categories of food items. For instance and without limitation, food tolerance scores may be organized by particular food categories such as vegetables, proteins, fats, fruits, grains, herbs, spices, beverages, and the like. Food tolerance scores may be organized by particular tolerance scores such as all food items that a user can enjoy without hesitation, all food items that a user should minimize, and all food items that a user should avoid. Food tolerance instruction set may include a numerical score containing a tolerance percentage for each food item. For instance and without limitation, food tolerance instruction set may include a numerical score on a scale from 1 to 100, with 1 being the least tolerable and 100 being the most tolerable. Each food item may contain a numerical score indicating a particular food tolerance level. For instance and without limitation, a food instruction set may include a food item such as kale having a food tolerance score of 20% while a food item such as green string beans having a food tolerance score of 75%. In an embodiment, food tolerance instruction set may be displayed on a graphical user interface using textual and/image representations. Food tolerance instruction set displayed on a graphical user interface may allow a user to touch and select a particular food item to open in a new window containing a photo of that particular food item with its own food tolerance score for that particular user. In an embodiment, food tolerance instruction set may be displayed on graphical user interface as pictures where a user can scroll through different pictures of food items and select a particular photograph of a food item to open in a new screen and display more detailed information about a particular food item.

With continued reference to FIG. 1, food analysis module 132 is configured to receive a user entry containing a food tolerance aversion input from a user client device 156 and filter the food tolerance instruction set 148 as a function of the user entry. A "user food tolerance aversion input" as used in this disclosure, includes a user input containing one or more food items that a user has an aversion to and prefers not to consume. An aversion to a food item may be due to an anaphylactic reaction to one or more food items, a food sensitivity to one or more food items, an aversion to one or more food items, a religious practice to not consume one or more food items, a dislike to one or more food items, a customary practice to not consume one or more food items, a dietary restriction to not consume one or more food items due to one or more health conditions or medical issues and the like. User client device 156 may include without limitation, a display in communication with processor 104; display may include any display as described herein. User client device 156 may include an additional computing device, such as a mobile device, laptop, desktop computer and the like. Food analysis module 132 filters the food tolerance instruction set 148 as a function of a user input. Filtering may include removing and/or limiting food items that contain a food tolerance aversion input within food tolerance instruction set 148.

With continued reference to FIG. 1, system 100 includes a graphical user interface 152. Graphical user interface 152 may include without limitation, a form or other graphical element having data entry fields, wherein a processor 104 may display data including for example food tolerance instruction set 148 to a user and/or medical professional such as a functional medicine doctor. Graphical user interface 152 may include data entry fields that may allow a user and/or informed advisor to enter free form textual inputs. Graphical user interface 152 may provide drop-down lists where a user and/or medical professional may be able to select one or more entries contained within a particular drop-down list. Food analysis module 132 displays on graphical user interface 152 output containing food tolerance instruction set 148 containing the food tolerance score. In an embodiment, a user and/or medical professional viewing a food tolerance instruction set 148 may select an organization scheme for the food tolerance instruction set 148 to be displayed on graphical user interface 152. Food tolerance instruction set 148 may be organized according to any organizational scheme as described above.

With continued reference to FIG. 1, system 100 includes a menu generator module 160, which may be implemented as any hardware and/or software module. Menu generator module 160 is designed and configured to receive the food tolerance instruction set 148 from the food analysis module 132; select a menu training set 164 from a menu database 168 as a function of the food tolerance instruction set 148 wherein the menu training set 164 correlates food tolerance scores to menu options 176; generate using a supervised machine-learning process a menu model 172 that receives the food tolerance instruction set 148 as an input and produces an output containing menu options 176 utilizing the menu training set 164; and display on the graphical user interface 152 located on the processor 104 the output containing menu options 176.

With continued reference to FIG. 1, menu generator module 160 selects a menu training set 164 from a menu database 168. Menu training set 164 correlates food tolerance scores to menu options 176. A "menu option" as used in this disclosure, includes a list of available dish choices that may be selected for a particular meal. A meal may include an eating occasion that occurs at certain time such as breakfast, lunch, dinner, and/or snacks. Menu option may include a description of food items that may be incorporated into particular dish choices. Dish choices include particular dishes that may be prepared with particular and distinctive ingredients and techniques. For instance and without limitation, a dish choice for breakfast may include an option such as oatmeal topped with walnuts and blueberries. In yet another non-limiting example, a dish choice for lunch may include an option such as a salad containing romaine lettuce and topped with turkey breast and avocado. Menu database 168 includes any data structure suitable for use as clustering database 120 as described above. Menu generator module 160 selects a menu training set 164 from menu database 168 as a function of food tolerance instruction set 148. For instance and without limitation, menu generator module 160 may select a menu training set 164 that includes a data entry containing a food tolerance for a vegetable such as spinach correlated to a menu option that includes a spinach salad if a food tolerance instruction set 148 contains spinach having a tolerance score of enjoy where a user is able to consume spinach without any resulting gastrointestinal symptoms. Menu generator module 160 may not select a menu training set 164 that includes a data entry containing a food tolerance for a fruit such as apricot correlated to a menu option that includes a fruit salad containing apricot if a food tolerance instruction set 148 contains apricot having a tolerance score of minimize or avoid.

With continued reference to FIG. 1, menu generator module 160 generates using a supervised machine-learning process a menu model 172 that receives the food tolerance instruction set 148 as an input and produces an output containing menu options 176 utilizing the menu training set 164. Menu model 172 includes any machine learning process that is a linear or polynomial regression algorithm, the menu model might be an equation; it might be a set of instructions to generate outputs based on inputs which is derived using the machine-learning algorithm, and the like. Supervised machine-learning process may include any of the supervised machine-learning processes as described above. Menu generator module 160 displays on graphical user interface 152 output containing menu options 176. Graphical user interface 152 includes any of the graphical user interface 152 as described above.

With continued reference to FIG. 1, system 100 includes a local selector module 180, which may be implemented as any hardware and/or software module. Local selector module 180 is designed and configured to receive a plurality of meal option inputs 184 from a meal preparer device 188 wherein the meal option inputs 184 contain available menu listings; receive the output containing menu options 176 from the menu generator module 160; generate a k-nearest neighbors algorithm 192 utilizing the plurality of meal option inputs 184 and the menu options 176; identify a plurality of compatible meal options 196 as a function of generating the k-nearest neighbor algorithm; and display the plurality of compatible meal options 196 on the graphical user interface 152 located on the processor 104.

With continued reference to FIG. 1, local selector module 180 is configured to receive a plurality of meal option inputs 184 from a meal preparer device 188 wherein the meal option inputs 184 contain available menu listings. A "meal option input" as used in this disclosure, includes data describing available meals that a user can order and purchase that are cooked and prepared from meal preparers. "Meal preparers" as used in this disclosure, include any participant involved in the preparation and/or cooking of meal options. Meal providers may include a restaurant such as a locally owned independently operating restaurant or a chain restaurant that is found at multiple locations. Meal providers may include a company that prepares pre-packaged meals. Meal providers may include a grocery store that prepares meals. Meal preparers may include restaurants located within grocery stores. Meal preparers may include chefs or cooks who prepare meals at home or in a private commercialized kitchen. Meal providers may include a chef or cook who prepares meals in a school or kitchen or space that the chef or cook rents out for example. Meal option inputs 184 include available menu listings. "Available menu listings" as used in this disclosure, include one or more dishes that a meal preparer has available for purchase by a user. Available menu listings may include one or more dishes for a particular meal such as breakfast, lunch, dinner, and/or snacks or may contain available items that can be purchased irrespective of what meal they relate to. For instance and without limitation, an available menu listing may contain an option such as yogurt parfait with berries for breakfast, seared salmon with asparagus for lunch, and shrimp scampi for dinner. Available menu listing may contain one or more dishes available for a particular meal, such as for breakfast available menu listing may include buckwheat pancakes, Mediterranean omelet, berry smoothie, or oatmeal topped with shredded coconut and flax seeds.

With continued reference to FIG. 1, local selector module 180 receives a plurality of meal option inputs 184 from a meal preparer device 188. Meal preparer device 188 may include any device suitable for use as user client device 156 as described above.

With continued reference to FIG. 1, local selector module 180 generates a k-nearest neighbor algorithm utilizing the plurality of meal option inputs 184 and the menu options 176. "K-nearest neighbor algorithm" as used in this disclosure, includes a lazy-learning method that utilizes feature similarity to analyze how closely out of sample features resemble training data to locate possible optimal vector outputs, classify possible optimal vector outputs, calculate an optimal vector output, and generate an optimal vector output. Generating a k-nearest neighbor algorithm utilizing a k-nearest neighbor algorithm may include specifying a K-value, selecting k entries in a database which are closest to the known sample, determining the most common classifier of the entries in the database, and classifying the known sample. A lazy-learning process and/or protocol, which may alternatively be referred to as a "lazy loading" or "call when needed" process and/or protocol, may be a process whereby machine-learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data. Heuristic may include selecting some number of highest-ranking associations and/or training data elements. Lazy learning may implement any suitable lazy learning algorithm, including without limitation, a K-nearest neighbors algorithm 192, a lazy naïve Bayes algorithm, or the like; persons skilled in the art, upon reviewing the entirety of this disclosure, will be aware of the various lazy-learning algorithms that may be applied to generate outputs as described in this disclosure, including without limitation lazy learning applications of machine-learning algorithms as described in further detail below. Generating k-nearest neighbor algorithm identifies a plurality of compatible meal options 196, which are displayed on a graphical user interface 152 located on a processor 104.

With continued reference to FIG. 1, local selector module 180 is configured to select a compatible meal options 196 from the plurality of compatible meal options 196. Local selector module 180 receives a user input from a user client device 156 containing a meal option element indicator. A "user meal option element indicator" as used in this disclosure, includes data describing one or more user preferences regarding compatible meal options 196. User preferences may include information such as how much money a user wishes to spend on a particular compatible meal option, how many meals a user may be ordering, certain restrictions a user may have as to particular sources of ingredients that may be utilized to prepare a meal option such as a preference for organic produce or free range meats, user habits such as how frequently a user consumes meals throughout the day, quality of ingredients that may be utilized such as cold pressed olive oil or non-genetically modified corn products and the like. Local selector module 180 generates a loss function utilizing the user input and the plurality of meal option inputs 184.

With continued reference to FIG. 1, mathematical expression may represent a loss function, where a "loss function" is an expression an output of which an optimization algorithm minimizes to generate an optimal result. As a non-limiting example, local selector module 180 may calculate variables reflecting scores relating to particular user meal option element indicators, calculate an output of mathematical expression using the variables, and select a meal option that produces an output having the lowest size, according to a given definition of "size," of the set of outputs representing each of the plurality of meal options; size may, for instance, included absolute value, numerical size, or the like. Selection of different loss functions may result in identification of different meal options as generating minimal outputs; for instance, where organic ingredients is associated in a first loss function with a large coefficient or weight, a meal option having a small coefficient or weight for organic ingredients may minimize the first loss function, whereas a second loss function wherein organic ingredients has a smaller coefficient but degree of variance from cost which has a larger coefficient may produce a minimal output for a different meal option having a larger organic ingredients but more closely hewing to cost.

With continued reference to FIG. 1, mathematical expression and/or loss function may be generated using a machine learning to produce loss function: i.e., regression. Mathematical expression and/or loss function be user-specific, using a training set composed of past user selections; may be updated continuously. Mathematical expression and/or loss function may initially be seeded using one or more user inputs as above. User may enter a new command changing mathematical expression, and then subsequent user inputs may be used to generate a new training set to modify the new expression.

With continued reference to FIG. 1, mathematical expression and/or loss function may be generated using machine learning using a multi-user training set. Training set may be created using data of a cohort of persons having similar demographic, religious, health, and/or lifestyle characteristics to user. This may alternatively or additionally be used to seed a mathematical expression and/or loss function for a user, which may be modified by further machine learning and/or regression using subsequent user selections of alimentary provision options. Loss function analysis may measure changes in predicted values versus actual values, known as loss or error. Loss function analysis may utilize gradient descent to learn the gradient or direction that a cost analysis should take in order to reduce errors. Loss function analysis algorithms may iterate to gradually converge towards a minimum where further tweaks to the parameters produce little or zero changes in the loss or convergence by optimizing weights utilized by machine learning algorithms. Loss function analysis may examine the cost of the difference between estimated values, to calculate the difference between hypothetical and real values. Local selector module 180 may utilize variables to model relationships between past interactions between a user and system 100 and compatible meal options 196. In an embodiment loss function analysis may utilize variables that may impact user interactions and/or compatible meal options 196. Loss function analysis may be user specific so as to create algorithms and outputs that are customize to variables for an individual user.

With continued reference to FIG. 1, local selector module 180 is configured to generate a k-means clustering algorithm utilizing the plurality of meal option inputs 184 and the menu options 176 and identify a compatible meal option as a function of generating the k-means clustering algorithm. "K-means clustering algorithm" as used in this disclosure, includes cluster analysis that partitions n observations or unclassified cluster data entries into k clusters in which each observation or unclassified cluster data entry belongs to the cluster with the nearest mean. Cluster data entry may include data entries selected from a clustering dataset. Cluster data entry may be received from a clustering database 120. "Cluster analysis" as used in this disclosure, includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering whereby each observation or unclassified cluster data entry belongs to a cluster or not. Cluster analysis may include soft clustering or fuzzy clustering whereby each observation or unclassified cluster data entry belongs to each cluster to a certain degree such as for example a likelihood of belonging to a cluster. Cluster analysis may include strict partitioning clustering whereby each observation or unclassified cluster data entry belongs to exactly one cluster. Cluster analysis may include strict partitioning clustering with outliers whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering whereby observations or unclassified cluster data entries that belong to a child cluster also belong to a parent cluster.

With continued reference to FIG. 1, local selector module 180 may select a specific number of groups or clusters to output, identified by the variable "k." Generating a k-means clustering algorithm includes assigning inputs containing unclassified data to a "k-group" or "k-cluster" based on feature similarity. Centroids of k-groups or k-clusters may be utilized to generate classified data entry clusters. Local selector module 180 by select "k" variable by calculating k-means clustering algorithm for a range of k values and comparing results. Local selector module 180 may compare results across different values of k as the mean distance between cluster data entries and cluster centroid. Local selector module 180 may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. Generating a k-means clustering algorithm includes generating initial estimates for k centroids which may be randomly generated or randomly selected from unclassified data input. K centroids may be utilized to define one or more clusters. Local selector module 180 may assign unclassified data to one or more k-centroids based on the squared Euclidean distance by first performing a data assigned step of unclassified data. Local selector module 180 may assign unclassified data to its nearest centroid based on the collection of centroids $c_i$ of centroids in set C. Unclassified data may be assigned to a cluster based on $\mathrm{argmin}_{c_i \ni C} \mathrm{dist}(c_i, x)^2$, where argmin includes argument of the minimum; $c_i$ includes a collection of centroids in a set C; and dist includes standard Euclidean distance. Local selector module 180 may then recompute centroids by taking mean of all cluster data entries assigned to a centroid's cluster. This may be calculated based on $c_i = 1/|S_i| \Sigma x_i \in S_i^{vi}$. Local selector module 180 may continue to repeat these calculations until a stopping criterion has been satisfied such as when cluster data entries do not change clusters, the sum of the distances have been minimized, and/or some maximum number of iterations has been reached. K-means clustering algorithm identifies a compatible meal option as a function of generating k-means clustering algorithm.

With continued reference to FIG. 1, local selector module displays the plurality of compatible meal options on a graphical user interface. A "compatible meal option" as used in this disclosure, includes any meal that accommodates a user's biological markers. Accommodates includes generating and selecting meal options that are based on a user's biological markers and body measurements as described throughout this disclosure. A compatible meal option contains food items that are considered superfoods, food items that can be enjoyed, as well as food items that should be minimized from a food tolerance instruction set. A compatible meal option does not contain food items that are considered food items to be avoided from a food tolerance instruction set.

Figure 2:
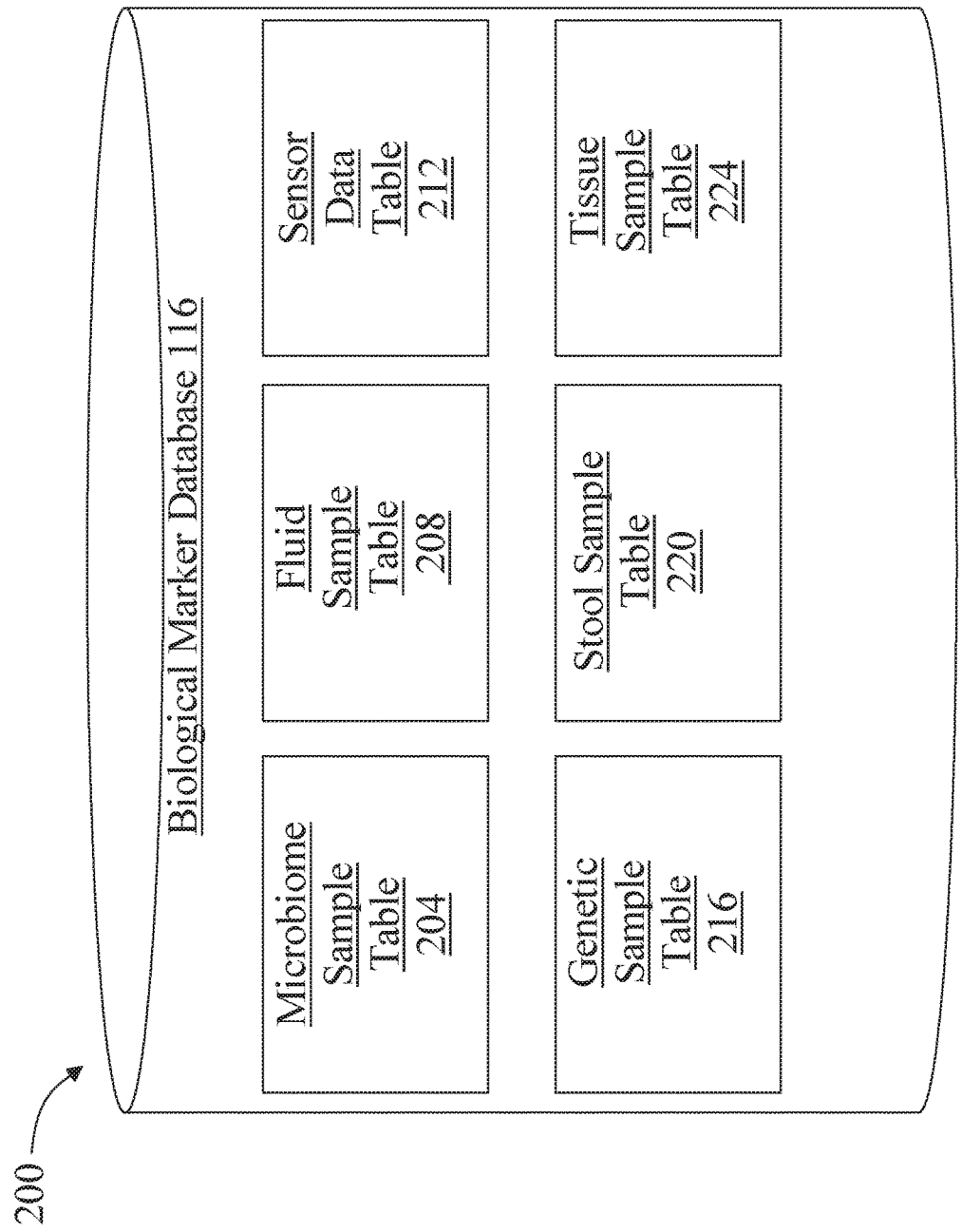
FIG. 2 is a block diagram illustrating an exemplary embodiment of a biological marker database.

Referring now to FIG. 2, an exemplary embodiment 200 of biological marker database 116 is illustrated. Biological marker database 116 may be implemented as any data structure suitable for use as clustering database 120 as described above in reference to FIG. 1. Biological marker database 116 may store one or more biological markers 112. One or more tables contained within biological marker database 116 may include microbiome sample table 204; microbiome sample table 204 may store one or more biological marker 112 relating to the microbiome. For instance and without limitation, microbiome sample table 204 may include results reflecting levels of a particular bacterial strain such as quantities of *Bifidobacterium* found in a user's gastrointestinal tract. One or more tables contained within biological marker database 116 may include fluid sample table 208; fluid sample table 208 may store one or more biological marker 112 obtained from a fluid sample. For instance and without limitation, fluid sample table 208 may include one or more entries containing results from fluids such as urine, saliva, sweat, tears, blood, mucus, cerebrospinal fluid, and the like analyzed for one or more biological marker 112. One or more tables contained within biological marker database 116 may include sensor data table 212; sensor data table 212 may include one or more biological marker 112 obtained from one or more sensors. For instance and without limitation, sensor data table 212 may include sleeping patterns of a user recorded by a sensor. One or more tables contained within biological marker database 116 may include genetic sample table 216; genetic sample table 216 may include one or more biological marker 112 containing one or more genetic sequences. For instance and without limitation, genetic sample table 216 may include a user's genetic sequence for a particular gene such as a sequence illustrating a positive breast cancer one (BRACA 1) gene. One or more tables contained within biological marker database 116 may include stool sample table 220; stool sample table 220 may include one or more biological marker 112 obtained from a stool sample. For instance and without limitation, stool sample table 220 may include a user's stool sample analyzed for the presence and/or absence of one or more parasites. One or more tables contained within biological marker database 116 may include tissue sample table 224; tissue sample table 224 may include one or more biological marker 112 obtained from one or more tissue samples. For instance and without limitation, tissue sample table 224 may include a breast tissue sample analyzed for the absence and/or presence of estrogen markers. Other tables not illustrated may include but are not limited to epigenetic, gut-wall, nutrients, and/or metabolism.

Figure 3:
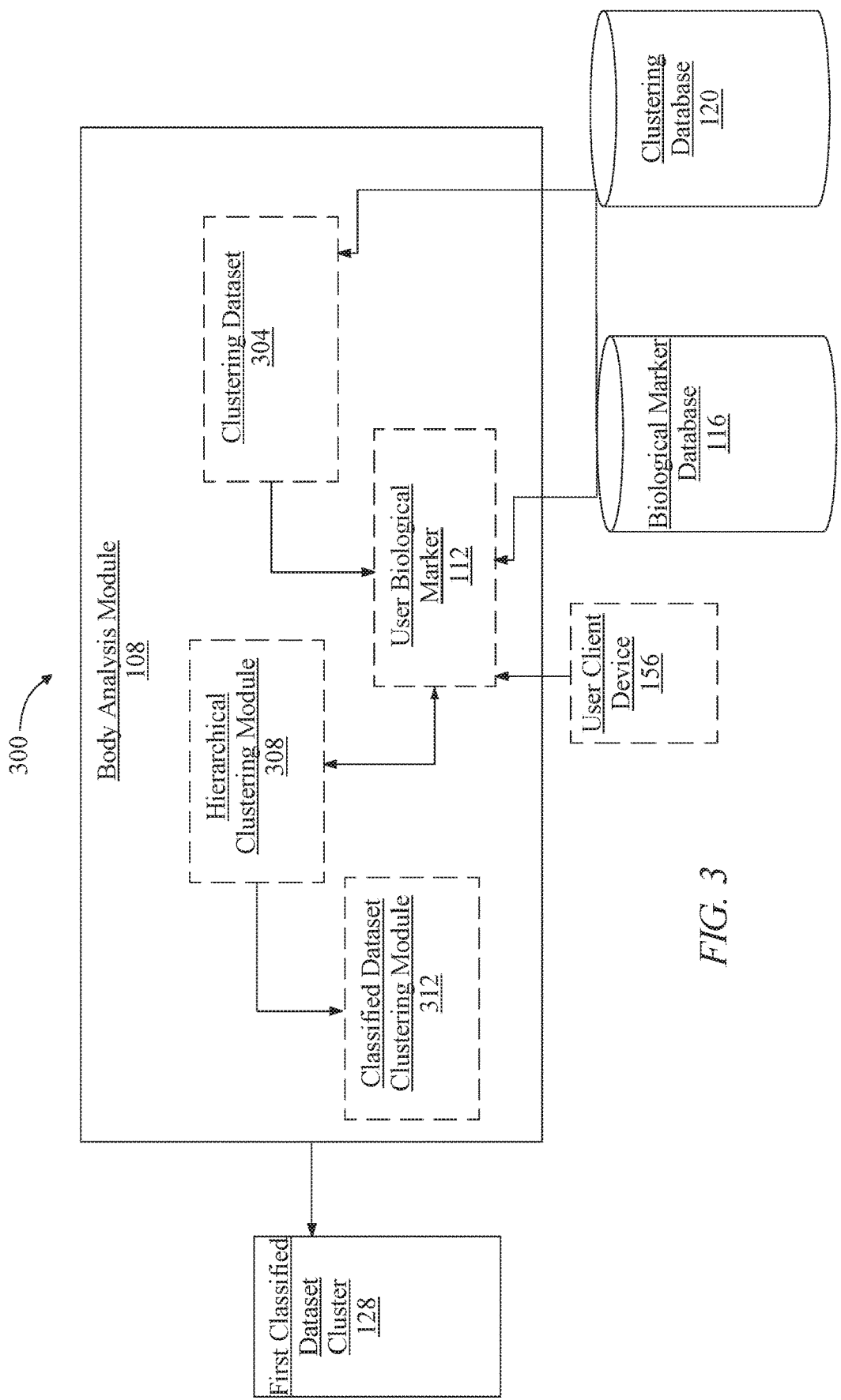
FIG. 3 is a block diagram illustrating an exemplary embodiment of a body analysis module.

Referring now to FIG. 3, an exemplary embodiment 300 of body analysis module 108 is illustrated. Body analysis module 108 may be implemented as any software and/or hardware module. Body analysis module 108 receives a user biological marker 112 containing a plurality of user body measurements. Body analysis module 108 may receive a user biological marker 112 from user client device 156. This may be performed utilizing any network methodology as described herein. Body analysis module 108 may receive a user biological marker 112 from biological marker database 116 as described above in more detail in reference to FIG. 2. For instance and without limitation, body analysis module 108 may receive from biological marker database 116a biological marker 112 such as a saliva sample analyzed for multiple user body measurements such as progesterone level, testosterone level, estrogen level, heavy metal toxicity, cortisol measurement, and thyroid level. In yet another non-limiting example, body analysis module 108 may receive from user client device 156 a user biological marker 112 such as results from a stool sample analyzed for multiple user body measurements including digestion markers such as chymotrypsin, putrefactive short-chain fatty acids, gut metabolic markers such as beneficial short-chain fatty acids with n-butyrate, beta-glucuronidase, fecal lactoferrin, and gut microbiology markers such as species of beneficial bacteria, additional bacteria, and mycology. In an embodiment, user body measurements include an element of user microbiome data, an element of user gut-wall data, and an element of user genetic data. For instance and without limitation, body analysis module 108 may receive a user biological marker 112 obtained from a finger prick blood sample that includes body measurements containing an element of user microbiome data such as an analysis of pathogenic bacterial found within the blood sample, an element of user gut-wall data such as a measurement of endotoxin lipopolysaccharide (LPS) found within the blood sample, and an element of user genetic data such as a reading of a user's level of DNA repair metabolites such as 8-OHdG levels.

With continued reference to FIG. 3, body analysis module 108 is configured to select a clustering dataset 304 from clustering database 120. Clustering database 120 may be implemented as any data structure as described above in more detail in reference to FIG. 1. Clustering dataset 304 includes a plurality of unclassified datapoints. Clustering dataset 304 may be stored in any suitable data and/or data type. For instance and without limitation, clustering dataset may include textual data such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as dataset may take; persons skilled in the art, upon reviewing the entirety of this disclosure, will be aware of various forms which may be suitable for use as dataset consistently with this disclosure.

With continued reference to FIG. 3, clustering dataset 304 may be stored as image data, such as for example an image of a particular food substance such as a photograph of a pear or an image of a steak. Image data may be stored in various forms including for example, joint photographic experts group (JPEG), exchangeable image file format (Exif), tagged image file format (TIFF), graphics interchange format (GIF), portable network graphics (PNG), netpbm format, portable bitmap (PBM), portable any map (PNM), high efficiency image file format (HEIF), still picture interchange file format (SPIFF), better portable graphics (BPG), drawn filed, enhanced compression wavelet (ECW), flexible image transport system (FITS), free lossless image format (FLIF), graphics environment manage (GEM), portable arbitrary map (PAM), personal computer exchange (PCX), progressive graphics file (PGF), gerber formats, 2 dimensional vector formats, 3 dimensional vector formats, compound formats including both pixel and vector data such as encapsulated postscript (EPS), portable document format (PDF), and stereo formats.

With continued reference to FIG. 3, datasets may be obtained from a plurality of sources. Clustering datasets 304 contained within clustering database 120 may contain a plurality of data entries, obtained for example, from patient medical records that have been stripped of identifying information. Clustering datasets 304 contained within clustering database 120 may be obtained from patient surveys who may be sampled in a variety of methods such as by phone, mail, internet and the like. Patient surveys may be distributed to patients across a breadth of geographical locations and may also be stripped of identifying information. Clustering datasets contained within clustering database 120 may be obtained from clinical data such as from facilities including nursing homes, hospitals, home health agencies, and the like.

With continued reference to FIG. 3, clustering dataset 304 contains a plurality of unclassified datapoints. "Unclassified datapoints" as used in this disclosure, include datapoints that have not been assigned, generated, and/or calculated category labels. Classification may include the process of predicting a class of given data entries. Classification may include using predictive modeling that approximates a mapping function from input variables to discrete output variables. Classification may be performed utilizing classification algorithms that include for example decision trees, naïve bayes, artificial neural networks, boosting, kernel methods, and/or k-nearest neighbors algorithm 192.

With continued reference to FIG. 3, body analysis module 108 may select a clustering dataset 304 by classifying a user body data element to a body dimension. Body dimension may include any of the body dimensions as described above in reference to FIG. 1. Body analysis module 108 may classify biological marker 112 to a body measurement utilizing any of the classification models as described above. Body analysis module 108 generates a classification label containing a body dimension label. For instance and without limitation, a biological marker 112 such as a blood sample analyzed for intracellular nutrient levels that include sodium, calcium, and potassium may be classified to contain a body dimension label that contains nutrients. Body analysis module 108 selects a clustering dataset from clustering database 120 by matching a body dimension label to a clustering dataset containing unclassified datapoints relating to the body dimension. For instance and without limitation, a body dimension label such as gut-wall integrity may be matched to a clustering dataset that contains unclassified datapoints that include measurements of markers of gut-wall integrity. In yet another non-limiting example, a body dimension label such as microbiome may be matched to a clustering dataset that contains unclassified datapoints that include measurements of the microbiome.

With continued reference to FIG. 3, body analysis module 108 may include hierarchical clustering module 308, which may be implemented as any hardware and/or software module. Hierarchical clustering module 308 is configured to generate a hierarchical clustering algorithm 124 using the clustering dataset and input. Hierarchical clustering algorithm 124 may include any of the hierarchical clustering algorithm 124 as described above in reference to FIG. 1. Hierarchical clustering module 308 outputs a definite number of classified dataset clusters each containing a clustering label. Clusters may be composed of one or more datapoints that have one or more shared similarities. A "clustering label" as used in this disclosure, includes descriptive labels for each cluster produced by a clustering algorithm. Clustering labels may be generated by calculating one or more algorithms that may produce an output that summarizes the topic of each clustering and distinguishes it from every other cluster. Clustering labels may be generated to reflect the one or more shared similarities of each datapoint contained within a particular cluster.

With continued reference to FIG. 3, body analysis module 108 may include classified dataset clustering module 312, which may be implemented as any hardware and/or software module. Classified dataset clustering module 312 may assign the plurality of user body measurements to a first classified dataset cluster 128 containing a cluster label. Classified dataset clustering module selects the first classified dataset cluster 128 containing the cluster label. Body analysis module 108 is configured to generate cluster labels indicating body dimension that datapoints relate to. Body analysis module 108 receives a plurality of user body measurements, generates a clustering algorithm using the user body measurements as input and outputting a plurality of cluster labels containing a body dimension. Clustering algorithm may include any clustering algorithm such as centroid based clustering, density based clustering, distribution based clustering, hierarchical clustering, k-means clustering, mean-shift clustering, density-based spatial clustering of applications with noise, expectation-maximization clustering using Gaussian mixture models, agglomerative hierarchical clustering, and the like. Body analysis module 108 selects a first classified dataset cluster 128 as a function of the body dimension. In an embodiment, expert input may be provided and stored within system 100 that may rank body dimensions by importance and indicates what body dimension needs to be addressed first. For instance and without limitation, expert input may dictate that a body dimension such as microbiome needs to be selected and addressed first before gut-wall integrity. In yet another non-limiting example, expert input may dictate that a body dimension such as nutrients needs to be selected and addressed first before metabolism.

Figure 4:
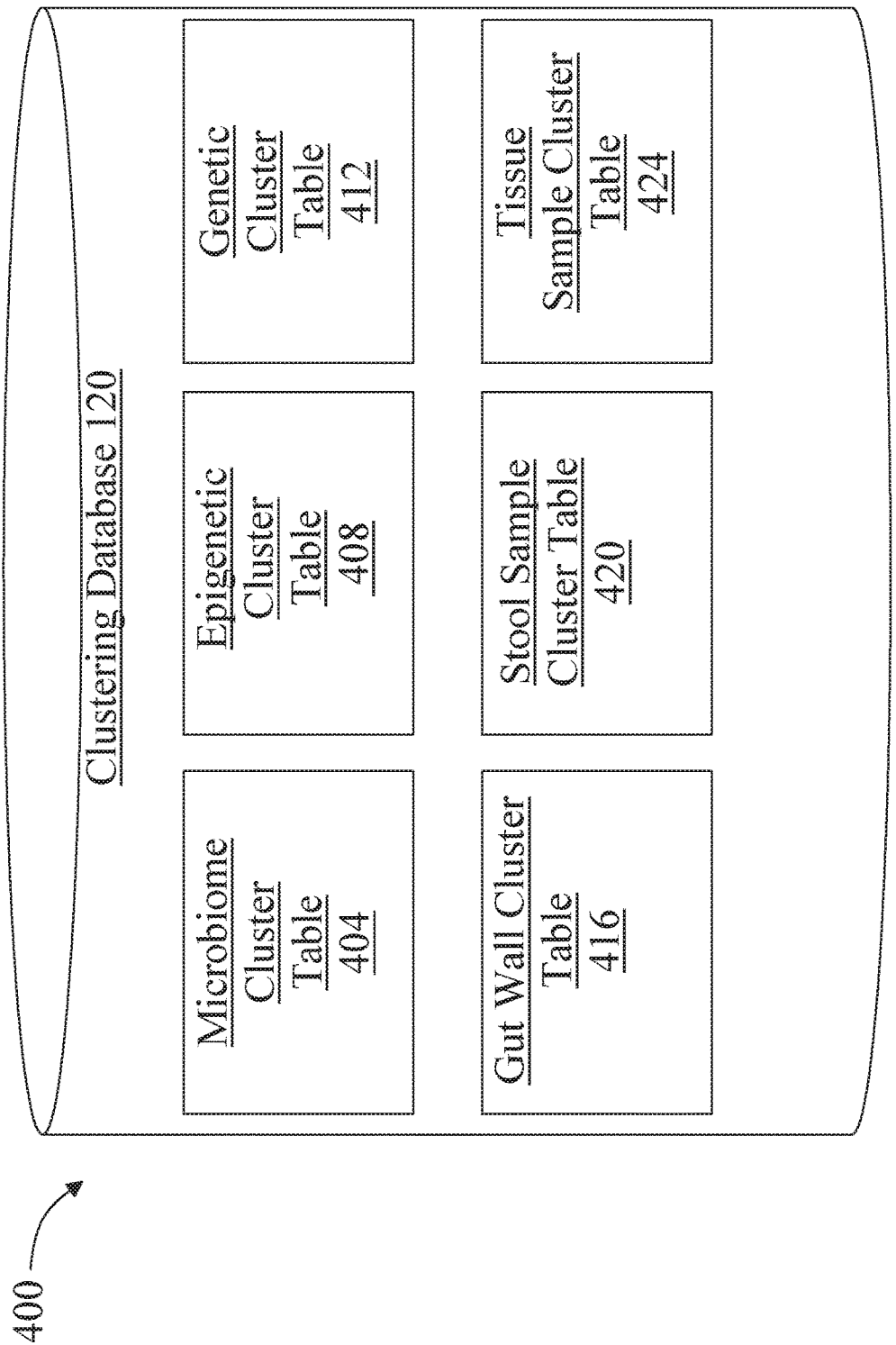
FIG. 4 is a block diagram illustrating an exemplary embodiment of a clustering database.

Referring now to FIG. 4, an exemplary embodiment 400 of clustering database 120 is illustrated. Clustering database 120 may be implemented as any data structure as described above. Clustering database 120 may store one or more clustering datasets, which may be organized according to datapoints contained within each dataset. One or more tables contained within clustering database 120 may include microbiome cluster table 404; microbiome cluster table 404 may include one or more clustering datasets related to the microbiome body dimension. One or more tables contained within clustering database 120 may include epigenetic cluster table 408; epigenetic cluster table 408 may include one or more datasets related to the epigenetic body dimension. One or more tables contained within clustering database 120 may include genetic cluster table 412; genetic cluster table 412 may include one or more datasets related to genetic body dimension. One or more tables contained within clustering database 120 may include gut-wall cluster table 416; gut-wall cluster table 416 may include one or more datasets related to gut-wall body dimension. One or more tables contained within clustering database 120 may include stool sample cluster table 420; stool sample cluster table 420 may include one or more datasets containing datapoints obtained from stool samples. One or more tables contained within clustering database 120 may include tissue sample cluster table 424; tissue sample cluster table 424 may include one or more datasets containing datapoints obtained from tissue samples. Other tables not illustrated may include but are not limited to nutrients cluster table, metabolism cluster table, fluid sample cluster table, and/or sensor cluster table.

Figure 5:
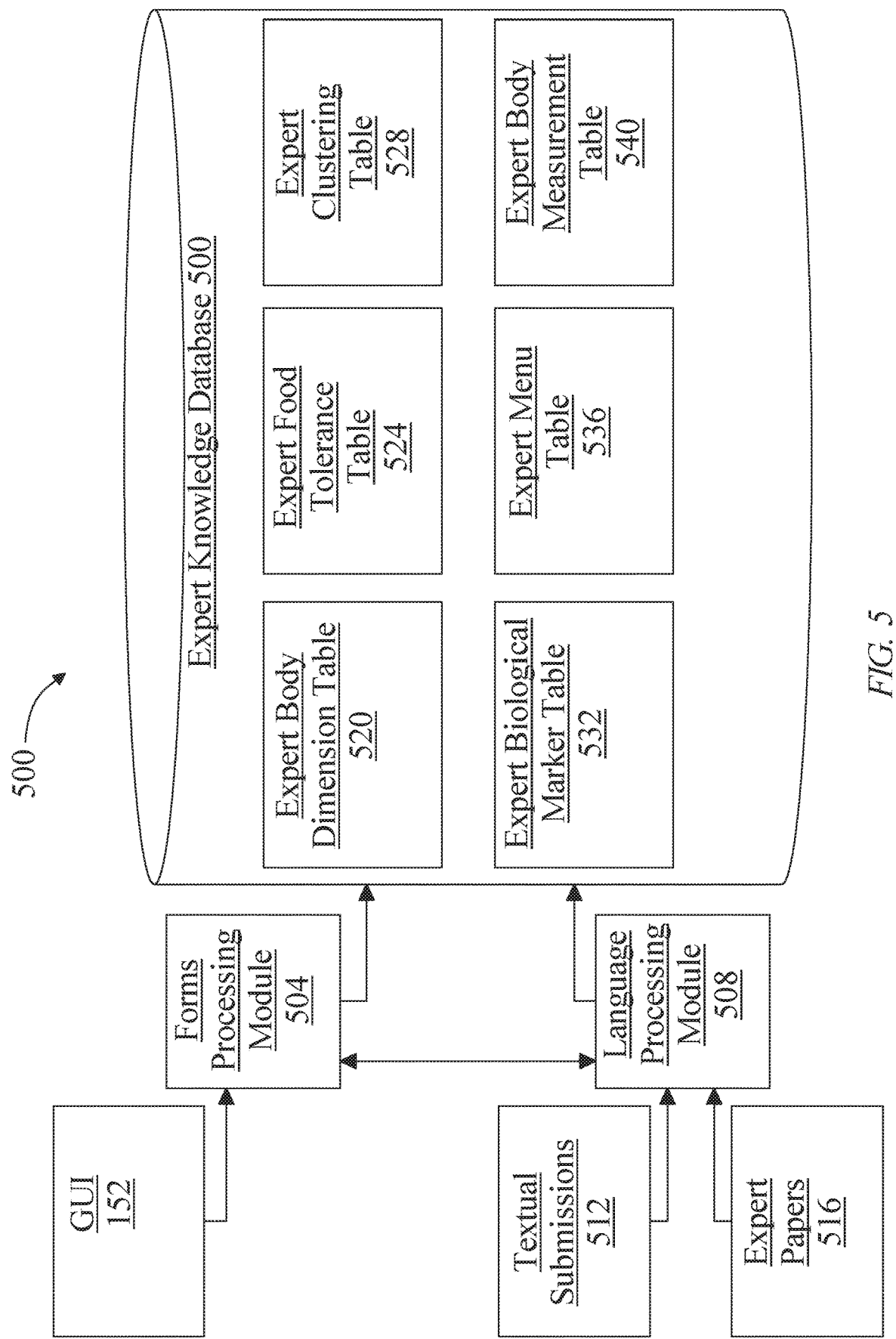
FIG. 5 is a block diagram illustrating an exemplary embodiment of an expert knowledge database.

Referring now to FIG. 5, an exemplary embodiment 500 of expert knowledge database is illustrated. Expert knowledge database may be implemented as any data structure as described above in reference to FIG. 1. One or more database tables may be linked to one another by, for instance, common column values. For instance, a common column between two tables of expert knowledge database may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data may be included in one or more tables.

With continued reference to FIG. 5, expert knowledge database includes a forms processing module 504 that may sort data entered in a submission via graphical user interface 152 by, for instance, sorting data from entries in the graphical user interface 152 to related categories of data; for instance, data entered in an entry relating in the graphical user interface 152 to a body dimension may be sorted into variables and/or data structures for storage of body dimensions, while data entered in an entry relating to a category of clustering data and/or an element thereof may be sorted into variables and/or data structures for the storage of, respectively, categories of clustering data. Where data is chosen by an expert from pre-selected entries such as drop-down lists, data may be stored directly; where data is entered in textual form, language processing module 508 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module 508 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 512, such as accomplished by filling out a paper or PDF form and/or submitting narrative information, may likewise be processed using language processing module 508. Data may be extracted from expert papers 516, which may include without limitation publications in medical and/or scientific journals, by language processing module 508 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

With continued reference to FIG. 5, one or more tables contained within expert knowledge database may include expert body dimension table 520; expert body dimension table 520 may include one or more data entries containing expert input regarding body dimensions. One or more tables contained within expert knowledge database may include expert food tolerance table 524; expert food tolerance table 524 may include one or more data entries containing expert input regarding food tolerance scores. One or more tables contained within expert knowledge database may include expert clustering table 528; expert clustering table 528 may include one or more data entries containing expert input regarding clustering datasets, clustering algorithms, clustering datapoints, and the like. One or more tables contained within expert knowledge database may include expert biological marker 112 table 532; expert biological marker 112 table 532 may include one or more data entries containing expert input regarding biological marker 112. One or more tables contained within expert knowledge database may include expert menu table 336; expert menu table 336 may include one or more data entries containing expert input regarding menus. One or more tables contained within expert knowledge database may include expert body measurement table 340; expert body measurement table 340 may include one or more data entries containing expert input regarding body measurements.

Figure 6:
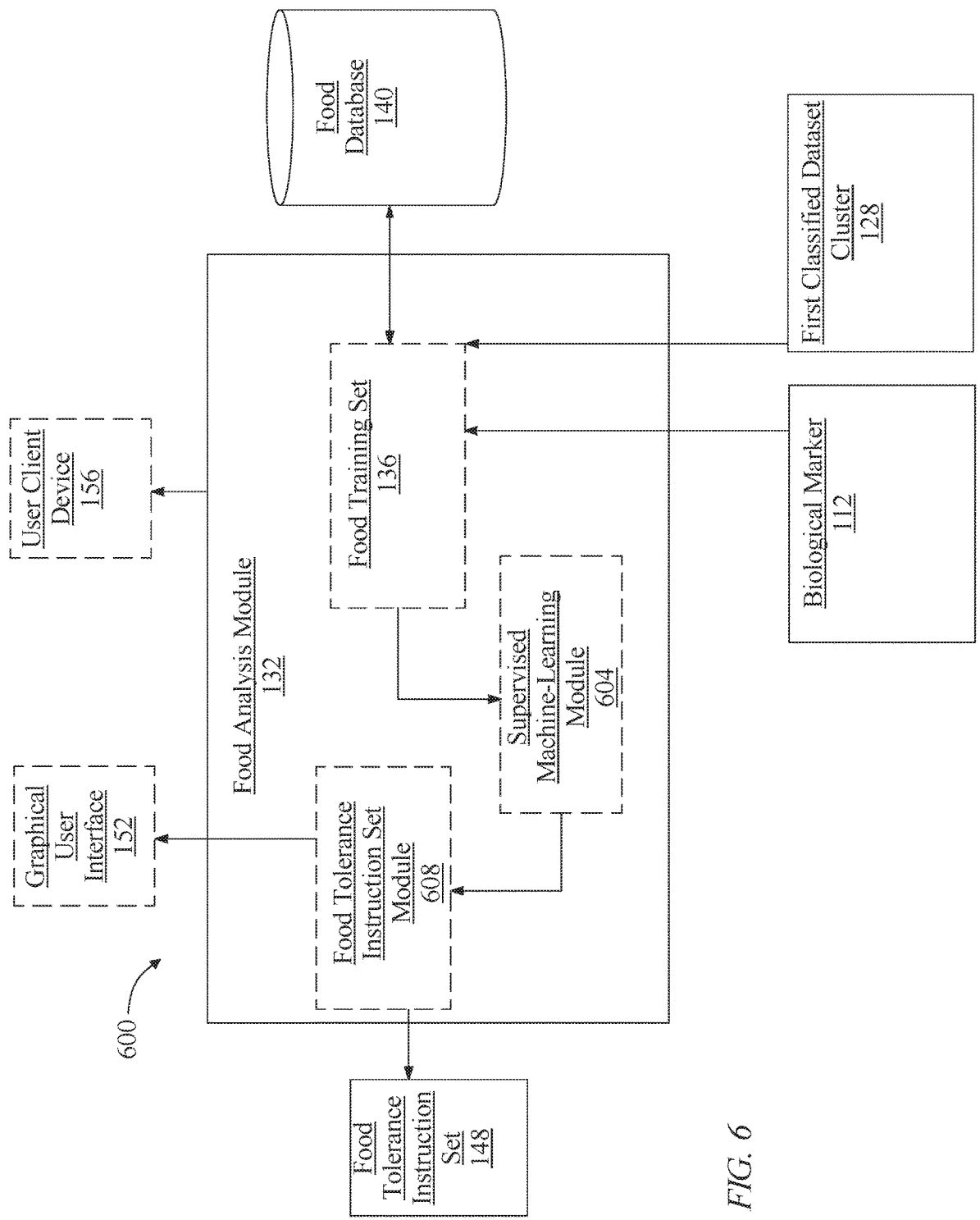
FIG. 6 is a block diagram illustrating an exemplary embodiment of a food analysis module.

Referring now to FIG. 6, an exemplary embodiment 600 of food analysis module 132 is illustrated. Food analysis module 132 may be implemented as any hardware and/or software module. Food analysis module 132 receives from body analysis module 108 the first classified dataset cluster 128 containing a cluster label and a user biological marker 112. Food analysis module 132 may receive a first classified data set cluster and a user biological marker 112 utilizing any network topography as described herein. Food analysis module 132 selects a food training set 136 from a food database 140 as a function of a user biological marker 112 wherein the food training set 136 correlates user body measurements to food tolerance scores. In an embodiment, food training set 136 may be organized within food training database by biological marker 112 as described in more detail below. Food analysis module 132 may select food training set 136 by matching a user biological marker 112 to a food training ser containing data entries that contain the same user biological marker 112 correlated to food tolerance scores. For instance and without limitation, food analysis module 132 may receive a user biological marker 112 that contains a body measurement such as a salivary estradiol level. In such an instance, food analysis module 132 may select a food training set 136 that includes a body measurement that includes a salivary estradiol level correlated to food tolerance scores. In an embodiment, food training set 136 may be organized according to body measurement and/or biological marker 112 as described in more detail below.

With continued reference to FIG. 6, food analysis module 132 may include a supervised machine-learning module 604, which may be implemented as any hardware and/or software module. Supervised machine-learning module 604 generates using a supervised machine-learning process a food model 144 that receives the plurality of user body measurements assigned to a first classified dataset cluster 128 containing a cluster label as an input and produces an output containing a food tolerance score. Supervised machine-learning processes may include any of the supervised machine-learning models as described above in reference to FIG. 1. Food tolerance score includes an indication of a user ability to tolerate a particular food item. For instance and without limitation, a supervised machine-learning process may be utilized to produce an output that contains food tolerance score for a user with a biological marker 112 such as breast cancer gene 2 (BRACA2) to contain a food tolerance score that includes foods a user can enjoy that are rich in glucosinolates such as broccoli and cauliflower, while food tolerance scores may indicate foods the user can avoid as being foods rich in trans-fats such as vegetable shortening, vegetable oil, fried foods, and canned frosting. In an embodiment, supervised-machine learning model may select a food model 144 from food database 140. Food model 144 may be pre-calculated and loaded into food database 140.

With continued reference to FIG. 6, food analysis module 132 may include food tolerance instruction set module 608, which may be implemented as any hardware and/or software module. Food tolerance instruction set module 608 generates a food tolerance instruction set 148 using the food tolerance scores. Food tolerance instruction set 148 includes data structure containing one or more food tolerance scores organized by particular categories of food items as described above in reference to FIG. 1. For instance and without limitation, food tolerance instruction set 148 may include food items categorized into categories that may include superfoods which contains food items that are the most beneficial, food items that can be enjoyed as frequently as a user desires, food items that can be consumed with particular customized limits, and foods that should be avoided completely. In yet another non-limiting example, food tolerance instruction set 148 may be categorized by groups of food items, such as food items classified as vegetables, food items classified as proteins, food items classified as fats, food items classified as fruits, food items classified as grains, food items classified as herbs, food items classified as spices, and food items classified as miscellaneous. Food analysis module 132 displays on a graphical user interface 152 located on a processor 104 the output produced by the food analysis module 132 containing the food tolerance instruction set 148 containing the food tolerance score. In an embodiment, a user may indicate and/or select on a graphical user interface 152 how a user wishes to view and have food items organized within a particular food tolerance instruction set 148. Food analysis module 132 is configured to receive a user entry from a user client device 156 containing a user food tolerance aversion input and filter a food tolerance instruction set 148 as a function of the user entry. A user food tolerance aversion may include a user input containing one or more food items that a user has an aversion to and prefers not to consume as described above in more detail in reference to FIG. 1. For instance and without limitation, a user food tolerance aversion input may include a user response that includes avoidance of blueberries and strawberries because a user does not like the taste of certain berries. In yet another non-limiting example, a user food tolerance aversion input may include a user response that includes avoidance of egg yolk and egg whites because user has a food sensitivity to egg products. In yet another non-limiting example, a user food tolerance aversion input may include a user response that includes avoidance of walnuts because user has a previously diagnosed immunoglobulin E (IGE) anaphylactic response to walnuts. In an embodiment, user food tolerance aversions may be stored locally in a database and may be retrieved from the database by food analysis module 132. Food analysis module 132 may filter food tolerance instruction set 148 by eliminating food items containing a user food tolerance aversion input from food tolerance instruction set 148. Filtering by food analysis module 132 may also include changing a food item containing a user food tolerance aversion to contain a food tolerance score to avoid.

Figure 7:
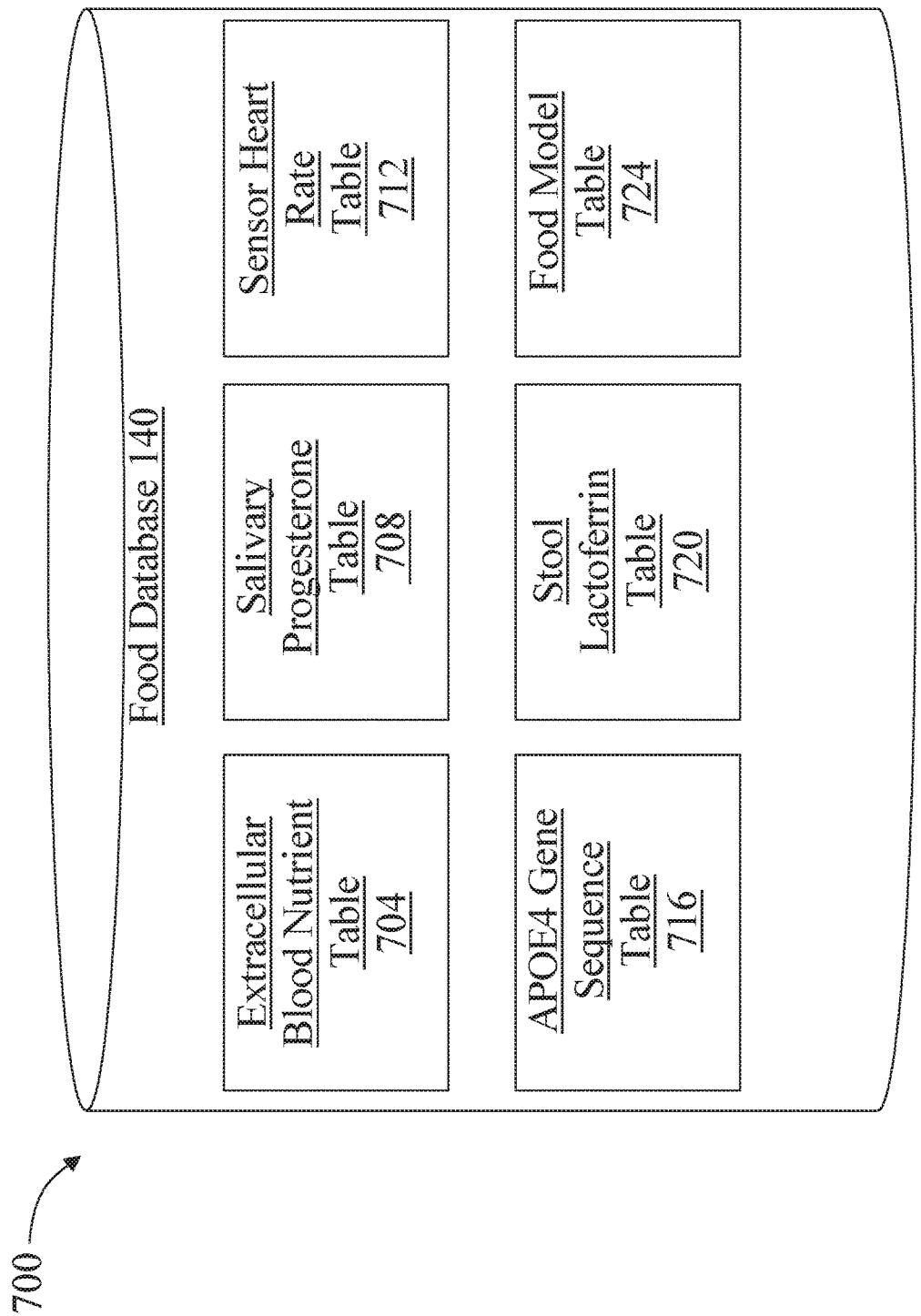
FIG. 7 is a block diagram illustrating an exemplary embodiment of a food database.

Referring now to FIG. 7, an exemplary embodiment 700 of food database 140 is illustrated. Food database 140 may be implemented as any data structure as described above in reference to FIG. 1. In an embodiment, one or more tables contained within food database 140 may be organized by body measurement. One or more tables contained within food database 140 may include extracellular blood nutrient table 704; extracellular nutrient table 704 may include one or more training sets containing body measurements that include but are not limited to extracellular blood nutrients correlated to food tolerance scores. One or more tables contained within food database 140 may include salivary progesterone table 708; salivary progesterone table 708 may include one or more training sets containing body measurements that include but are not limited to salivary progesterone levels correlated to food tolerance scores. One or more tables contained within food database 140 may include sensor heart rate table 712; sensor heart rate table 712 may include one or more training sets containing body measurements that include but are not limited to sensor heart rates correlated to food tolerance scores. One or more tables contained within food database 140 may include APOE4 gene sequence table 716; APOE4 gene sequence table 716 may include one or more training sets containing body measurements that include but are not limited to APOE4 gene sequences correlated to food tolerance scores. One or more tables contained within food database 140 may include stool lactoferrin table 720; stool lactoferrin table 720 may include one or more training sets containing body measurements that include but are not limited to stool levels of lactoferrin correlated to food tolerance scores. One or more tables contained within food database 140 may include food model 144 table 724; food model 144 table 724 may include one or more food model 144.

Figure 8:
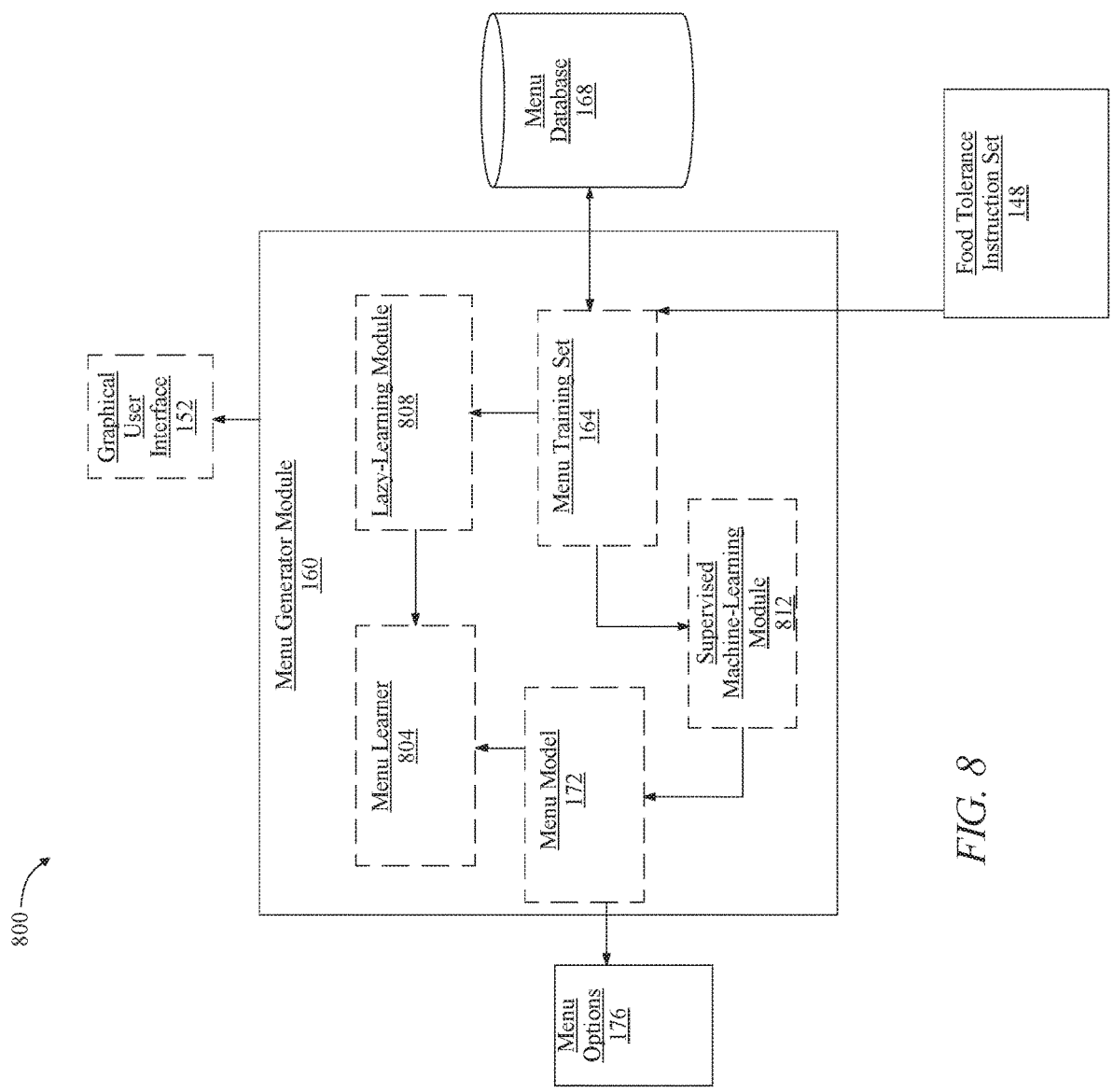
FIG. 8 is a block diagram illustrating an exemplary embodiment of a menu generator module.

Referring now to FIG. 8, an exemplary embodiment 800 of menu generator module 160 is illustrated. Menu generator module 160 may be implemented as any hardware and/or software module. Menu generator module 160 receives a food tolerance instruction set 148 from food analysis module 132. Menu generator module 160 may receive a food tolerance instruction set 148 utilizing any hardware and/or software module. Menu generator module 160 selects a menu training set 164 from a menu database 168 as a function of a food tolerance instruction set 148 wherein the menu training set 164 correlates food tolerance scores to menu options 176. Menu generator module 160 may include menu learner 804 which may be implemented as any hardware and/or software module. Menu learner 804 may aid menu generator module 160 in selecting menu training set 164 from menu database 168. Menu learner 804 is configured to receive a model training set correlating food tolerance instruction set 148 to menu training set 164 and generate using a supervised machine-learning process and the model training set a training set model that receives the food tolerance instruction set 148 as an input and produces an output containing menu training set 164. Model training set includes any training set as described herein. Training set model includes any machine-learning model, including any supervised machine-learning process as described above. Menu learner 804 may learn and continue to update selections of menu training set 164 for particular food tolerance instruction set 148. Menu learner may generate using a supervised machine-learning process and the model training set a training set model. Supervised machine-learning process may include any of the supervised machine-learning processes as described above in reference to FIG. 1. Model training set and/or training set model may be stored within menu database 168. Training set models may be precalculated and loaded into menu database 168.

With continued reference to FIG. 8, menu generator module 160 may include a lazy-learning module 808 which may be implemented as any hardware and/or software module. Lazy-learning module 808 may be utilized to select a menu training set 164 by executing a lazy learning process as a function of a model training set and a food tolerance instruction set 148 and producing an output containing menu training set 164. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at a menu training set 164 associated with a food tolerance instruction set 148, using model training set. As a non-limiting example, an initial heuristic may include a ranking of menu training set 164 according to relation to a test type of a food tolerance instruction set 148, one or more categories of food items identified in test type of a food tolerance instruction set 148, and/or one or more values detected in a food tolerance instruction set 148; ranking may include, without limitation, ranking according to significance scores of associations between food items and food tolerance instruction set 148, for instance as calculated as described above. Heuristic may include selecting some number of highest-ranking associations and/or food tolerance scores. Lazy learning module may alternatively or additionally implement any suitable "lazy learning" algorithm, including without limitation a K-nearest neighbors algorithm 192, a lazy naïve Bayes algorithm, or the like; persons skilled in the art, upon reviewing the entirety of this disclosure, will be aware of various lazy-learning algorithms that may be applied to generate menu training set 164 as described in this disclosure, including without limitation lazy learning applications of machine-learning algorithms.

With continued reference to FIG. 8, menu generator module 160 may include supervised machine-learning module 812. Supervised machine-learning module 812 may be implemented as any hardware and/or software module. Supervised machine-learning module 812 generates using a supervised machine-learning process a menu model 172 that receives the food tolerance instruction set 148 as an input and produces an output containing a plurality of menu options 176 utilizing the menu training set 164. Menu model 172 includes any machine-learning model as described above. Menu model 172 may include any supervised machine-learning model as described above. Menu model 172 includes any machine learning process that is a linear or polynomial regression algorithm, the menu model may include an equation; it may be a set of instructions to generate outputs based on inputs which is derived using the machine-learning algorithm, and the like. Supervised machine-learning process include any of the supervised machine-learning processes as described above in reference to FIG. 1. Menu generator module 160 may select menu model 172 from menu database 168. Menu model 172 may be precalculated and stored within menu database 168. A plurality of menu options 176 include a list of available dish choices that may be selected for a particular meal as described above in more detail in reference to FIG. 1. Menu options 176 may include options that a user may cook at home or options that a user may order from particular food preparers as described above in more detail in reference to FIG. 1. Menu generator module 160 displays a plurality of menu options 176 on a graphical user interface 152 located on a graphical user interface 152 located on a processor 104.

Figure 9:
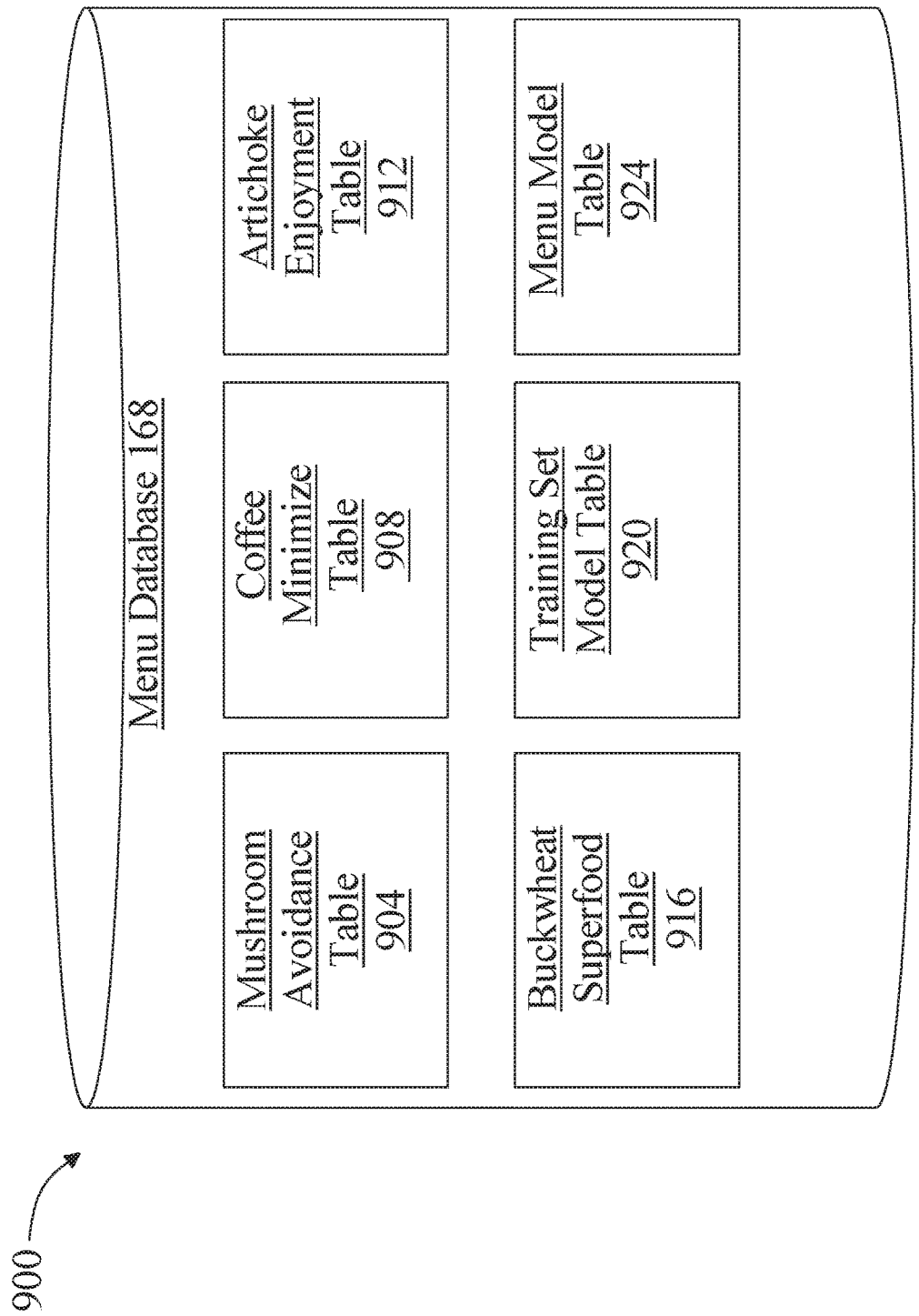
FIG. 9 is a block diagram illustrating an exemplary embodiment of a menu database.

Referring now to FIG. 9, an exemplary embodiment 900 of menu database 168 is illustrated. Menu database 168 may be implemented as any data structure suitable for use as clustering database 120 as described above in reference to FIG. 1. Menu database 168 may store menu training set 164, menu model 172, training set models, and/or model training sets. One or more tables contained within menu database 168 may include mushroom avoidance table 904; mushroom avoidance table 904 may include menu training set 164 that include mushroom food items containing a food tolerance score of avoidance. One or more tables contained within menu database 168 may include coffee minimize table 908; coffee minimize table 908 may include menu training set 164 that include coffee food items containing a food tolerance score of minimize. One or more tables contained within menu database 168 may include artichoke enjoyment table 912; artichoke enjoyment table 912 may include menu training set 164 that include artichoke food items containing a food tolerance score of enjoyment. One or more tables contained within menu database 168 may include buckwheat superfood table 916; buckwheat superfood table 916 may include menu training set 164 that include buckwheat food items containing a food tolerance score of superfood. One or more tables contained within menu database 168 may include training set model table 920; training set model table 920 may include one or more model training sets and/or training set models. One or more tables contained within menu database 168 may include menu model 172 table 924; menu model 172 table 924 may include one or more menu model 172.

Figure 10:
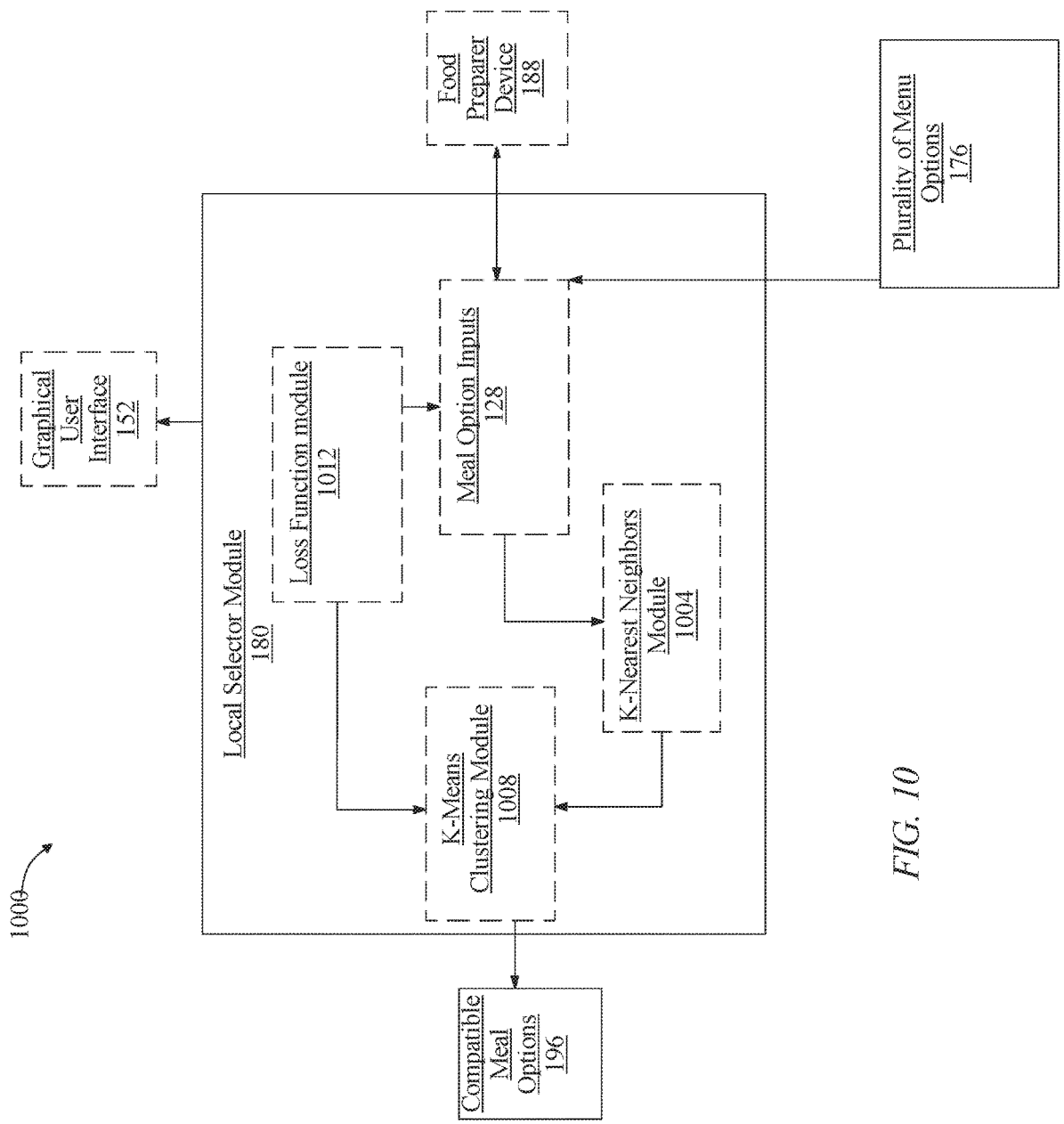
FIG. 10 is a block diagram illustrating an exemplary embodiment of a local selector module.

Referring now to FIG. 10, an exemplary embodiment 1000 of local selector module 180 is illustrated. Local selector module 180 may be implemented as any hardware and/or software module. Local selector module 180 is configured receive a plurality of meal option inputs 184 from a meal preparer device 188 wherein the meal option inputs 184 contain available menu listings. Local selector module is configured to receive an element of user geolocation data and receive a plurality of meal option inputs from a meal preparer device 188 related to the element of user geolocation data. An "element of user geolocation data" as used in this disclosure, includes any data describing where a particular user is located at any given moment. An element of user geolocation data may be obtained from a user device, from a global positioning system (GPS) input, cell-tower triangulation data and the like. Local selector module may receive a plurality of meal option inputs from a meal preparer device 188 related to an element of user geolocation data. Meal option inputs may be related to an element of user geolocation data when meal option inputs are received from meal preparer device 188 who may provide meals in a location where user is currently located as indicated by user's element of geolocation data. For instance and without limitation, an element of user geolocation data may indicate that a user is currently located in Houston, Tex. In such an instance, local selector module may receive a plurality of meal option inputs from meal preparer device 188 located within Houston, Tex. or from meal preparer device 188 that provide meals to users located within Houston, Tex. Meal option inputs 184 may be received utilizing any network topography as described herein. Meal option inputs 184 include data describing available meals that a user can order and purchase that are cooked and prepared from meal preparers. Meal preparers include any of the meal preparers as described above in reference to FIG.

1. Local selector module 180 receives a plurality of menu options 176 from menu generator module 160 utilizing any network methodology as described herein.

With continued reference to FIG. 10, local selector module 180 may include a k-nearest neighbors module 1004. K-nearest neighbors (KNN) module 1004 may be implemented as any hardware and/or software module. KNN module 1004 is configured to generate a k-nearest neighbors algorithm 192 utilizing the plurality of meal option inputs 184 and the plurality of menu options 176. K-nearest neighbors algorithm 192 includes a lazy-learning process as described above in more detail in reference to FIG. 1. KNN module may modify meal options inputs and a plurality of menu options 176 by representing meal option inputs 184 and a plurality of menu options 176 as vectors. Vectors may include mathematical representations of meal option inputs 184 and a plurality of menu options 176. Vectors may include n-tuple of values which may represent a measurement or other quantitative value associated with a given category of data, or attribute. Vectors may be represented in n-dimensional space using an axis per category of value represented in n-tuple of values, such that a vector has a geometric direction characterizing the relative quantities of attributes in the n-tuple as compared to each other. In an embodiment, KNN module 1004 may calculate an initial heuristic ranking association between inputs and elements of meal option inputs 184 and a plurality of menu options 176. Initial heuristic may include selecting some number of highest-ranking associations and/or training data elements. KNN module 1004 may perform one or more processes to modify and/or format meal option inputs 184 and a plurality of menu options 176. Meal option inputs 184 and a plurality of menu options 176 may contain "N" unique features, whereby a dataset contained within meal option inputs 184 and a plurality of menu options 176 may be represented as a vector may contain a vector of length "N" whereby entry "I" of the vector represents that data point's value for feature "I." Each vector may be mathematically represented as a point in "R^N." For instance and without limitation, KNN module 1004 may modify entries contained within meal option inputs 184 and a plurality of menu options 176 to contain consistent forms of a variance. KNN module 1004 performs K-nearest neighbor algorithm by classifying datasets contained within meal option inputs 184 and a plurality of menu options 176. Meal option inputs 184 and a plurality of menu options 176 may be represented as an "M×N" matrix where "M" is the number of data points contained within meal option inputs 184 and a plurality of menu options 176 and "N" is the number of features contained within meal option inputs 184 and a plurality of menu options 176. Classifying datasets contained within meal option inputs 184 and a plurality of menu options 176 may include computing a distance value between an item to be classified such as a meal option and each dataset contained within meal option inputs 184 and a plurality of menu options 176 which may be represented as a vector. A value of "k" may be pre-determined or selected that will be used for classifications. In an embodiment, value of "k" may be selected as an odd number to avoid a tied outcome. In an embodiment, value of "k" may be decided by KNN module 1004 arbitrarily or value may be cross validated to find an optimal value of "k.". KNN module 1004 may then select a distance metric that will be used in K-nearest neighbor algorithm. In an embodiment, KNN module 1004 may utilize Euclidean distance which may be measure distance by subtracting the distance between a training data point and the datapoint to be classified such as a particular meal option. In an embodiment, Euclidean distance may be calculated by a formula represented as:

$$E(x, y) = \sqrt{\sum_{i=0}^{n}(xi - yi)^2}.$$

In an embodiment, KNN module 1004 may utilize metric distance of cosine similarity which may calculate distance as the difference in direction between two vectors which may be represented as: similarity=cos θ=A×B÷∥A∥∥B∥. After selection of "k" value, and selection of distance measurement by KNN module 1004, KNN module 1004 may partition in "R^N" into sections. Sections may be calculated using the distance metric and the available data points contained within meal option inputs 184 and a plurality of menu options 176. KNN module 1004 may calculate a plurality of optimal vector output; in such an instance, where a plurality of matching entries are returned, optimal vector output may be obtained by aggregating matching entries including any suitable method for aggregation, including component-wise addition followed by normalization component-wise calculation of arithmetic means, or the like. KNN module 1004 identifies a plurality of compatible meal options 196 as a function of generating a k-nearest neighbor algorithm.

With continued reference to FIG. 10, local selector module 180 may include k-means clustering module 1008. K-means clustering module may be implemented as any hardware and/or software module. K-means clustering module is configured to generate a k-means clustering algorithm utilizing the meal option inputs 184 and the plurality of menu options 176. K-means clustering module 1008 receives clustering dataset as input and outputs a definite number of classified data entry clusters that each contain cluster data entries. K-means clustering algorithm module 1008 may determine k-value that will set a fixed number of classified data entry clusters as outputs utilizing any of the methods as described above in reference to FIG. 1. In an embodiment, k-value may be selected based generating k-means clustering algorithm repeatedly until a k-value is averaged and selected. In yet another non-limiting example, a k-value may be selected based on a particular clustering dataset that may be best suited for a particular k-value. K-means clustering module 1008 receives as input unclassified clustering dataset. Unclassified clustering dataset may include any of the unclassified clustering dataset as described above in more detail in reference to FIG. 1. K-means clustering algorithm module 1008 outputs classified data entry clusters. Data entry clusters may be classified by k-means clustering algorithm module 1008 using predictive modeling that approximates a mapping function from input variables to discrete output variables. Classification may be performed utilizing classification algorithms that include for example decision trees, naïve bayes, artificial neural networks, boosting, kernel methods, and/or k-nearest neighbors algorithm 192. K-means clustering module 1008 may generate a soft k-means clustering algorithm wherein a "soft k-means clustering algorithm" as used in this disclosure includes a k-means clustering algorithm where a cluster data entry may be selected and/or assigned to multiple clusters of the definite number of classified data entry cluster. For instance and without limitation, k-means clustering algorithm module may generate a soft k-means clustering algorithm that has a k-value of seven and where a particular cluster data entry may be selected and assigned to three of the seven classified data entry cluster. K-means clustering algorithm module may generate a hard k-means clustering algorithm wherein a "hard k-means clustering algorithm" as used in this disclosure includes a k-means clustering algorithm where a cluster data entry may be selected to be assigned to one cluster of the definite number of classified data entry cluster. For instance and without limitation, k-means clustering module may generate a hard k-means clustering algorithm that has a k-value of seven and where a particular cluster data entry may be selected and assigned to one of the seven classified data entry cluster. K-means clustering algorithm 136 module may select a hard k-means algorithm and/or a soft k-means algorithm based on expert input as described in more detail below. In an embodiment, k-means clustering algorithm module may select a hard k-means algorithm and/or a soft k-means algorithm based on learned associations between clustering dataset and classified data entry outputs such as by learned associations such as from a clustering learner.

With continued reference to FIG. 10, local selector module may include loss function module. Loss function module may be implemented as any hardware and/or software module. Loss function module 1012 is configured to receive a user input from a user client device wherein a user input includes a meal option element indicator, generate a loss function utilizing the user input and the plurality of meal option inputs, minimize the loss function, and select a compatible meal option from the plurality of compatible meal options as a function of minimizing the loss function. Meal option element indicator includes any of the meal option element indicators as described above in reference to FIG. 1. For instance and without limitation, meal option element may include an indicator describing how much money a user is willing to pay for a particular compatible meal or how much money a user has budgeted for a particular month's worth of compatible meals. Meal option element may include a particular cooking preference such as an indication that a user prefers a meal preparer to prepare a compatible meal using Mediterranean Sea salt as opposed to table salt. Meal option element may include an indicator about particular cooking methods a user prefers such as a user who prefers a steak to be cooked medium rare or a soup to be prepared in a raw form. Loss function module generates a loss function utilizing any of the methods as described above in reference to FIG. 1. Loss function module minimizes the loss function and selects a compatible meal option as a function of minimizing the loss function.

Figure 11:
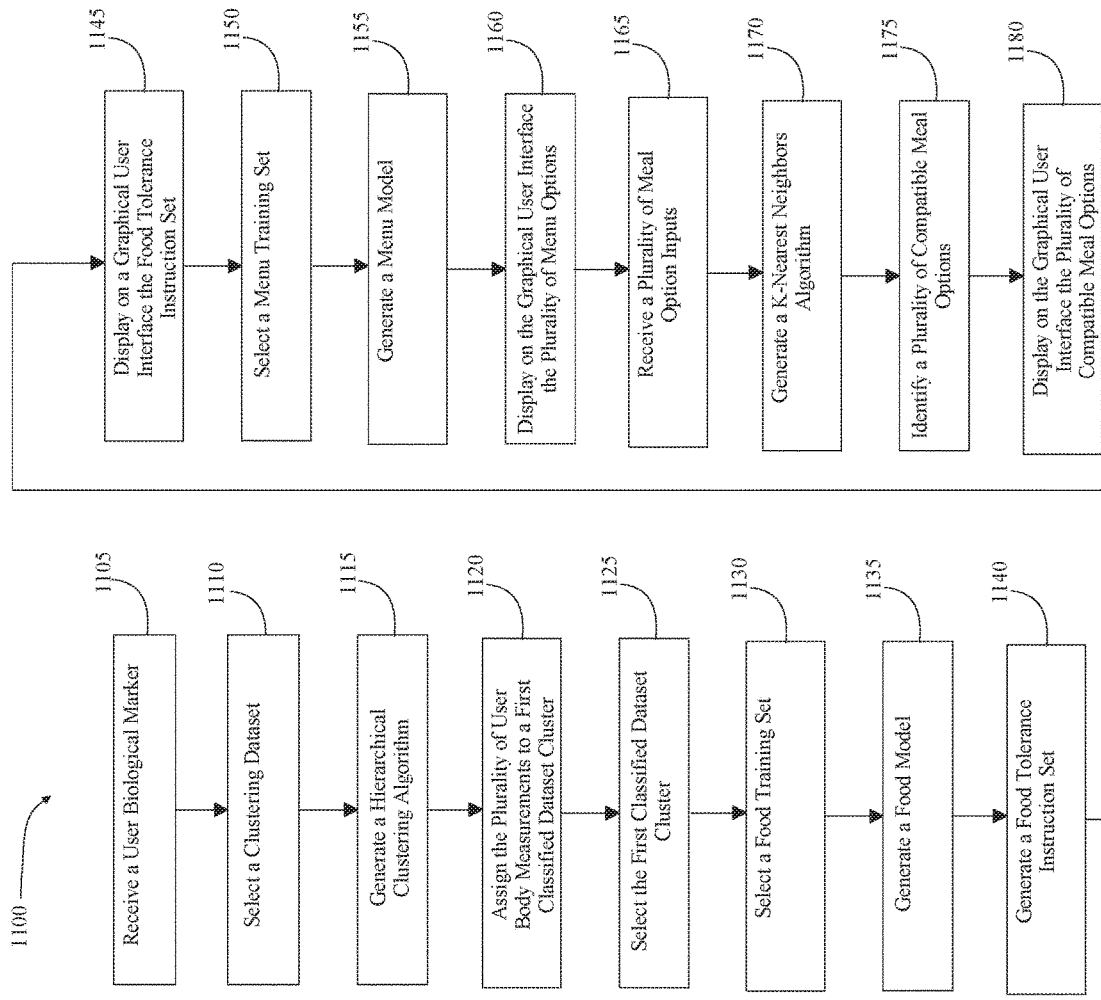
FIG. 11 is a process flow diagram illustrating an exemplary embodiment of a method of identifying compatible meal options.

Referring now to FIG. 11, an exemplary embodiment of a method 1100 of identifying compatible meal options is illustrated. At step 1105 a processor receives a user biological marker wherein the user biological marker contains a plurality of user body measurements. A user biological marker may include any of the user biological markers as described above in reference to FIGS. 1-10. User body measurements may include any of the user body measurements as described above in reference to FIGS. 1-10. In an embodiment, a plurality of user body measurements may include at least a microbiome body measurement, at least a gut-wall body measurement and at least a genetic body measurement as described above in more detail in reference to FIG. 1. A microbiome body measurement includes any of the microbiome body measurements as described above in more detail in reference to FIG. 1. A gut-wall body measurement includes any of the gut-wall body measurements as described above in more detail in reference to FIG. 1. A genetic body measurement includes any of the genetic body measurements as described above in more detail in reference to FIG. 1.

With continued reference to FIG. 11, at step 1110 a processor selects a clustering dataset from a clustering database wherein the clustering dataset further comprises a plurality of unclassified datapoints. Selecting a clustering dataset may be performed utilizing any of the methods as described above in reference to FIGS. 1-10. Selecting a clustering dataset includes classifying a biological marker to a body dimension, generating a classification label containing a body dimension label, and selecting a clustering dataset as a function of matching the body dimension label to a clustering dataset containing unclassified datapoints related to the body dimension label. This may be performed utilizing any of the methods as described above in reference to FIGS. 1-10. Body dimension may include any of the body dimensions described above in reference to FIG. 1.

With continued reference to FIG. 11, at step 1115 a processor generates a hierarchical clustering algorithm using the clustering dataset as input and wherein the hierarchical clustering algorithm outputs a definite number of classified dataset clusters each containing a cluster label. Generating a hierarchical clustering algorithm may be performed utilizing any of the methods as described above in reference to FIGS. 1-11.

With continued reference to FIG. 11, at step 1120 a processor assigns the plurality of user body measurements to a first classified dataset cluster containing a cluster label. Assigning a plurality of user body measurements to a first classified dataset cluster containing a cluster label may be performed utilizing any of the methods as described above in reference to FIGS. 1-11.

With continued reference to FIG. 11, at step 1125 a processor selects the first classified dataset cluster containing the cluster label. Selecting a first classified dataset cluster may include generating cluster labels that contain body dimensions. In an embodiment, a processor may receive a plurality of user body measurements, generate a clustering algorithm using the user body measurements as input and wherein the clustering algorithm outputs a plurality of cluster labels containing a body dimension, and select a first classified dataset cluster as a function of a body dimension. In an embodiment, experts may provide input as to particular body dimension labels and hierarchy of selecting a particular first classified dataset cluster containing a particular body dimension label.

With continued reference to FIG. 11, at step 1130 a processor selects a food training set from a food database as a function of the user biological marker wherein the food training set correlates user body measurements to food tolerance scores. Processor may select a food training set utilizing any of the methods as described above in reference to FIGS. 1-10.

With continued reference to FIG. 11, at step 1135 a processor generates using a supervised machine-learning process a food model that receives the first assigned user body data element as an input and produces an output containing a food tolerance score. Supervised machine-learning process may include any of the supervised machine-learning processes as described above in reference to FIG. 1. Food model may include any of the food models as described above in reference to FIGS. 1-10. In an embodiment, a food model may be pre-calculated and loaded into food database and selected by a processor from food database.

With continued reference to FIG. 11, at step 1140 a processor generates a food tolerance instruction set using the food tolerance score. Food tolerance instruction set may include any of the food tolerance instruction sets as described above in reference to FIGS. 1-10. Generating a food tolerance instruction set may be done utilizing any of the methods as described above in reference to FIGS. 1-10. Food tolerance instruction set may be generated by receiving a user entry from a user client device containing a food tolerance aversion input and filtering a food tolerance instruction set as a function of a user input. Food tolerance aversion may include any of the food tolerance aversions as described above in reference to FIGS. 1-10.

With continued reference to FIG. 11, at step 1145 a processor displays on a graphical user interface the output containing the food tolerance instruction set containing the food tolerance score. Food tolerance instruction set may be displayed by particular categories of tolerability and/or food items as described above in more detail in reference to FIGS. 1-10.

With continued reference to FIG. 11, at step 1150 a processor selects a menu training set from a menu database as a function of the food tolerance instruction set wherein the menu training set correlates food tolerance scores to menu options. Menu training data includes any of the menu training data as described above in reference to FIGS. 1-10. Menu training data may be selected by receiving a model training set correlating food tolerance instruction sets to menu training sets and generating using a supervised machine-learning process and the model training set a training set model that receives a food tolerance instruction set as input and produces an output containing menu training set. This may be performed utilizing any of the methods as described above in reference to FIGS. 1-10. Menu training set may also be selected by executing a lazy learning process as a function of model training set and food tolerance instruction set and producing an output containing menu training set. This may be performed utilizing any of the methods as described above in reference to FIGS. 1-10.

With continued reference to FIG. 11, at step 1155 a processor generates using a supervised machine-learning process a menu model that receives the food tolerance instruction set as an input and produces an output containing a plurality of menu options utilizing the menu training set. Supervised machine-learning process may include any of the supervised machine-learning processes as described above in reference to FIGS. 1-10. Menu model may include any of the menu models as described above in reference to FIGS. 1-10. In an embodiment, menu models may be precalculated and preloaded into menu database. A processor may select a menu model from menu database.

With continued reference to FIG. 11, at step 1160 a processor displays on the graphical user interface the output containing the plurality of menu options. This may be performed utilizing any of the methods as described above in reference to FIGS. 1-11.

With continued reference to FIG. 11, at step 1165 a processor receives a plurality of meal option inputs from a meal preparer device 188 wherein the meal option inputs contain available menu listings. A processor may receive a plurality of meal option inputs utilizing any network methodology as described herein. Meal option inputs include any of the meal-option inputs as described above in reference to FIGS. 1-10.

With continued reference to FIG. 11, at step 1170 a processor generates a k-nearest neighbors algorithm utilizing the plurality of meal option inputs and the plurality of menu options. K-nearest neighbors algorithm includes any of the k-nearest neighbors algorithm as described above in reference to FIGS. 1-10. K-nearest neighbors algorithm may be generated utilizing any of the methods as described above in reference to FIGS. 1-10. A processor may also be configured to identify a plurality of compatible meal options by generating a k-means clustering algorithm utilizing a plurality of menu options and meal option inputs and identify a compatible meal option as a function of generating the k-means clustering algorithm. K-means clustering algorithm includes any of the k-means clustering algorithms as described above in reference to FIGS. 1-10.

With continued reference to FIG. 11, at step 1175 a processor identifies a plurality of compatible meal options as a function of generating the k-nearest neighbor algorithm. In an embodiment, a processor may be configured to select a compatible meal option from a plurality of compatible meal options. A processor is configured to receive a user input from a user client device where the user input includes a meal option element indicator. Meal option element indicator includes any of the meal option element indicators as described above. For instance and without limitation, meal option element indicator may include a user entry regarding how much money a user is willing to spend for a particular meal or how soon a user would like a meal prepared and delivered. A processor generates a loss function utilizing a user input and a plurality of meal option inputs. A processor minimizes the loss function and selects a compatible meal option from the plurality of compatible meal options as a function of minimizing the loss function.

With continued reference to FIG. 11, at step 1180 a processor displays the plurality of compatible meal options on the graphical user interface. This may be performed utilizing any of the methods as described above in reference to FIGS. 1-10.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 12:
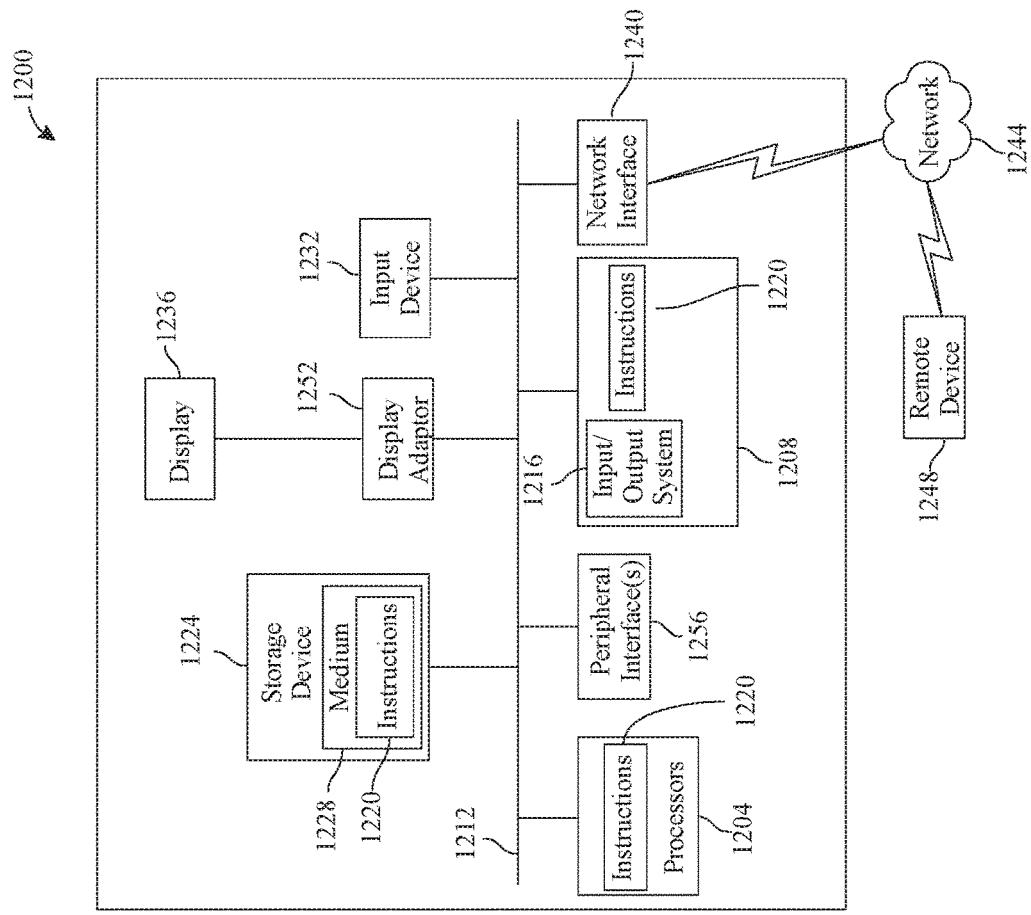
FIG. 12 is a block diagram of a computing system that can be used to implement any one or more of the methodologies disclosed herein and any one or more portions thereof.

FIG. 12 shows a diagrammatic representation of one embodiment of a computing device in the exemplary form of a computer system 1200 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1200 includes a processor 104 1204 and a memory 1208 that communicate with each other, and with other components, via a bus 1212. Bus 1212 may include any of several types of bus structures including, but not limited to, a memory bus, a memory controller, a peripheral bus, a local bus, and any combinations thereof, using any of a variety of bus architectures.

Memory 1208 may include various components (e.g., machine-readable media) including, but not limited to, a random access memory component, a read only component, and any combinations thereof. In one example, a basic input/output system 1216 (BIOS), including basic routines that help to transfer information between elements within computer system 1200, such as during start-up, may be stored in memory 1208. Memory 1208 may also include (e.g., stored on one or more machine-readable media) instructions (e.g., software) 1220 embodying any one or more of the aspects and/or methodologies of the present disclosure. In another example, memory 1208 may further include any number of program modules including, but not limited to, an operating system, one or more application programs, other program modules, program data, and any combinations thereof.

Computer system 1200 may also include a storage device 1224. Examples of a storage device (e.g., storage device 1224) include, but are not limited to, a hard disk drive, a magnetic disk drive, an optical disc drive in combination with an optical medium, a solid-state memory device, and any combinations thereof. Storage device 1224 may be connected to bus 1212 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1224 (or one or more components thereof) may be removably interfaced with computer system 1200 (e.g., via an external port connector (not shown)). Particularly, storage device 1224 and an associated machine-readable medium 1228 may provide nonvolatile and/or volatile storage of machine-readable instructions, data structures, program modules, and/or other data for computer system 1200. In one example, software 1220 may reside, completely or partially, within machine-readable medium 1228. In another example, software 1220 may reside, completely or partially, within processor 104 1204.

Computer system 1200 may also include an input device 1232. In one example, a user of computer system 1200 may enter commands and/or other information into computer system 1200 via input device 1232. Examples of an input device 1232 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1232 may be interfaced to bus 1212 via any of a variety of interfaces (not shown) including, but not limited to, a serial interface, a parallel interface, a game port, a USB interface, a FIREWIRE interface, a direct interface to bus 1212, and any combinations thereof. Input device 1232 may include a touch screen interface that may be a part of or separate from display 1236, discussed further below. Input device 1232 may be utilized as a user selection device for selecting one or more graphical representations in a graphical interface as described above.

A user may also input commands and/or other information to computer system 1200 via storage device 1224 (e.g., a removable disk drive, a flash drive, etc.) and/or network interface device 1240. A network interface device, such as network interface device 1240, may be utilized for connecting computer system 1200 to one or more of a variety of networks, such as network 1244, and one or more remote devices 1248 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1244, may employ a wired and/or a wireless mode of communication. In general, any network topology may be used. Information (e.g., data, software 1220, etc.) may be communicated to and/or from computer system 1200 via network interface device 1240.

Computer system 1200 may further include a video display adapter 1252 for communicating a displayable image to a display device, such as display device 1236. Examples of a display device include, but are not limited to, a liquid crystal display (LCD), a cathode ray tube (CRT), a plasma display, a light emitting diode (LED) display, and any combinations thereof. Display adapter 1252 and display device 1236 may be utilized in combination with processor 104 1204 to provide graphical representations of aspects of the present disclosure. In addition to a display device, computer system 1200 may include one or more other peripheral output devices including, but not limited to, an audio speaker, a printer, and any combinations thereof. Such peripheral output devices may be connected to bus 1212 via a peripheral interface 1256. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for identifying compatible meal options the system comprising a processor wherein the processor further comprises:
    a body analysis module wherein the body analysis module is further configured to:
        receive a user biological marker, wherein the user biological marker contains a plurality of user body measurements including an element of microbiome data, an element of physical user gut-wall data, and an element of user genetic data;
        select a clustering dataset from a clustering database wherein the clustering dataset further comprises a plurality of unclassified datapoints;
        generate a hierarchical clustering algorithm using the clustering dataset as input, wherein the hierarchical clustering algorithm outputs a definite number of classified dataset clusters each containing a cluster label;
        assign the plurality of user body measurements to a first classified dataset cluster containing a first cluster label; and
        select the first classified dataset cluster containing the first cluster label;
    a food analysis module wherein the food analysis module is further configured to:
        receive from the body analysis module the first classified dataset cluster containing the first cluster label and the user biological marker;
        select a food training set from a food database as a function of the user biological marker wherein the food training set correlates the element of microbiome data, the element of physical user gut-wall data, and the element of user genetic data to numerical food tolerance scores;
        generate using a supervised machine-learning process a food model that receives the assigned plurality of user body measurements as an input and produces an output containing a numerical food tolerance score utilizing the food training set;
        generate a food tolerance instruction set using the numerical food tolerance score; and
        display on a graphical user interface located on the processor the output containing the food tolerance instruction set;
    a menu generator module wherein the menu generator module is further configured to:
        receive the food tolerance instruction set from the food analysis module;
        select a menu training set from a menu database as a function of the food tolerance instruction set wherein the menu training set correlates numerical food tolerance scores to menu options;
        generate using a supervised machine-learning process a menu model that receives the food tolerance instruction set as an input and produces an output containing a plurality of menu options utilizing the menu training set; and
        display on the graphical user interface located on the processor the output containing the plurality of menu options; and
    a local selector module wherein the local selector module is further configured to:
        receive a plurality of meal option inputs from at least a meal preparer device wherein the meal option inputs contain available menu listings;
        receive the output containing the plurality of menu options from the menu generator module;
        generate a k-nearest neighbors algorithm utilizing the plurality of meal option inputs and the plurality of menu options;
        identify a plurality of compatible meal options as a function of generating the k-nearest neighbor algorithm; and
        display the plurality of compatible meal options on the graphical user interface located on the processor.

2. The system of claim 1, wherein the plurality of user body measurements further comprises at least a microbiome body measurement and at least a genetic body measurement.

3. The system of claim 1, wherein selecting a clustering dataset further comprises:
    classifying a biological marker to a body dimension;
    generating a classification label containing a body dimension label; and
    selecting a clustering dataset as a function of matching the body dimension label to a clustering dataset containing unclassified datapoints related to the body dimension label.

4. The system of claim 1, wherein selecting a first classified dataset cluster containing a first cluster label further comprises:
    receiving the plurality of user body measurements;
    generating a clustering algorithm using the user body measurements as input and wherein the clustering algorithm outputs a plurality of cluster labels containing a body dimension; and
    selecting the first classified dataset cluster as a function of the body dimension.

5. The system of claim 1, wherein generating the food tolerance instruction set further comprises:
    receiving a user entry from a user client device containing a user food tolerance aversion input; and filtering the food tolerance instruction set as a function of the user entry.

6. The system of claim 1, wherein selecting a menu training set further comprises:
receiving a model training set correlating food tolerance instruction sets to menu training sets; and
generating using a supervised machine-learning process and the model training set a training set model that receives the food tolerance instruction set as an input and produces an output containing menu training set.

7. The system of claim 6 further comprising executing a lazy learning process as a function of the model training set and the food tolerance instruction set and producing an output containing menu training set.

8. The system of claim 1, wherein the local selector module is further configured to:
receive a user input from a user client device wherein the user input further comprises a meal option element indicator;
generate a loss function utilizing the user input and the plurality of meal option inputs; minimize the loss function; and
select a compatible meal option from the plurality of compatible meal options as a function of minimizing the loss function.

9. The system of claim 1, wherein the local selector module is further configured to:
receive an element of user geolocation data; and
receive a plurality of meal option inputs from at least a meal preparer device related to the element of user geolocation data.

10. The system of claim 1, wherein the local selector module is further configured to:
generate a k-means clustering algorithm utilizing the plurality of menu options and the plurality of meal option inputs; and
identify a compatible meal option as a function of generating the k-means clustering algorithm.

11. A method of identifying compatible meal options the method comprising:
receiving by a processor a user biological marker wherein the user biological marker contains a plurality of user body measurements including an element of microbiome data, an element of physical user gut-wall data, and an element of user genetic data;
selecting by the processor a clustering dataset from a clustering database wherein the clustering dataset further comprises a plurality of unclassified datapoints;
generating by the processor a hierarchical clustering algorithm using the clustering dataset as input and wherein the hierarchical clustering algorithm outputs a definite number of classified dataset clusters each containing a cluster label;
assigning by the processor the plurality of user body measurements to a first classified dataset cluster containing a first cluster label;
selecting by the processor the first classified dataset cluster containing the first cluster label;
selecting by the processor a food training set from a food database as a function of the user biological marker wherein the food training set correlates the element of microbiome data, the element of physical user gut-wall data, and the element of user genetic data to numerical food tolerance scores;
generating by the processor using a supervised machine-learning process a food model that receives the assigned plurality of user body measurements as an input and produces an output containing a numerical food tolerance score utilizing the food training set;
generating by the processor a food tolerance instruction set using the numerical food tolerance score;
displaying by the processor on a graphical user interface the output containing the food tolerance instruction set containing the numerical food tolerance score;
selecting by the processor a menu training set from a menu database as a function of the food tolerance instruction set wherein the menu training set correlates numerical food tolerance scores to menu options;
generating by the processor using a supervised machine-learning process a menu model that receives the food tolerance instruction set as an input and produces an output containing a plurality of menu options utilizing the menu training set;
displaying by the processor on the graphical user interface the output containing the plurality of menu options;
receiving by the processor a plurality of meal option inputs from at least a meal preparer device wherein the meal option inputs contain available menu listings;
generating by the processor a k-nearest neighbors algorithm utilizing the plurality of meal option inputs and the plurality of menu options;
identifying by the processor a plurality of compatible meal options as a function of generating the k-nearest neighbor algorithm; and
displaying by the processor the plurality of compatible meal options on the graphical user interface.

12. The method of claim 11, wherein the plurality of user body measurements further comprises at least a microbiome body measurement and at least a genetic body measurement.

13. The method of claim 11, wherein selecting a clustering dataset further comprises:
classifying a biological marker to a body dimension;
generating a classification label containing a body dimension label; and
selecting a clustering dataset as a function of matching the body dimension label to a clustering dataset containing unclassified datapoints related to the body dimension label.

14. The method of claim 11, wherein selecting a first classified dataset cluster containing the cluster label further comprises:
receiving the plurality of user body measurements;
generating a clustering algorithm using the plurality of user body measurements as input and wherein the clustering algorithm outputs a plurality of cluster labels containing a body dimension; and
selecting a first classified dataset cluster as a function of the body dimension.

15. The method of claim 11, wherein generating the food tolerance instruction set further comprises:
receiving a user entry from a user client device containing a user food tolerance aversion input; and
filtering the food tolerance instruction set as a function of the user entry.

16. The method of claim 11, wherein selecting a menu training set further comprises:
receiving a model training set correlating food tolerance instruction sets to menu training sets; and
generating using a supervised machine-learning process and the model training set a training set model that receives the food tolerance instruction set as an input and produces an output containing menu training set.

17. The method of claim 16 further comprising executing a lazy learning process as a function of the model training set and the food tolerance instruction set and producing an output containing menu training set.

18. The method of claim 11, further comprising:

receiving, by a processor, a user input from a user client device wherein the user input further comprises a meal option element indicator;

generating, by a processor, a loss function utilizing the user input and the plurality of meal option inputs;

minimizing, by the processor, the loss function; and selecting, by a processor, a compatible meal option from the plurality of compatible meal options as a function of minimizing the loss function.

19. The method of claim 11, further comprising:

receiving, by the processor, an element of user geolocation data; and receiving, by the processor, a plurality of meal option inputs from at least a meal preparer device related to the element of user geolocation data.

20. The method of claim 11, further comprising:

generating, by the processor, a k-means clustering algorithm utilizing the plurality of menu options and the meal option inputs; and identifying, by the processor, a compatible meal option as a function of generating the k-means clustering algorithm.

* * * * *